(12) United States Patent
Sasagawa et al.

(10) Patent No.: US 9,045,446 B2
(45) Date of Patent: Jun. 2, 2015

(54) METHOD FOR PRODUCING EPOXY COMPOUND

(71) Applicant: Arakawa Chemical Industries, Ltd., Osaka-shi (JP)

(72) Inventors: Naoki Sasagawa, Tsukuba (JP); Kiyoshi Takumi, Osaka (JP); Yoichiro Ezaki, Tsukuba (JP)

(73) Assignee: ARAKAWA CHEMICAL INDUSTRIES, LTD., Osaka-Shi (JP)

( * ) Notice: Subject to any disclaimer, the term of this patent is extended or adjusted under 35 U.S.C. 154(b) by 0 days.

(21) Appl. No.: 13/934,078

(22) Filed: Jul. 2, 2013

(65) Prior Publication Data

US 2014/0073806 A1  Mar. 13, 2014

(30) Foreign Application Priority Data

Jul. 5, 2012  (JP) .................. 2012-151133

(51) Int. Cl.
*C07D 301/12* (2006.01)

(52) U.S. Cl.
CPC .................... *C07D 301/12* (2013.01)

(58) Field of Classification Search
USPC ........................................................ 549/531
See application file for complete search history.

(56) References Cited

U.S. PATENT DOCUMENTS 6,310,232 B1  10/2001  Ofori et al.

FOREIGN PATENT DOCUMENTS

| JP | 2003-192679 | A |   | 7/2003 |
| JP | 2004-115455 | A |   | 4/2004 |
| JP | 2007-181833 | A |   | 7/2007 |
| JP | 2007181833  |   | * | 7/2007 |
| JP | 2008-246287 | A |   | 10/2008 |
| JP | 2010-070480 | A |   | 4/2010 |
| JP | 2010070480  |   | * | 4/2010 |

OTHER PUBLICATIONS

Sato, K., et al., A halid-free method for olefin epoxidation with 30% hydrogen peroxide, Bull. Chem. Soc. Jpn., 1997, 70, pp. 905-915.
Sato, K., et al., A practical method for epodication of terminal olefins with 30% hydrogen peroxide under halide-free conditions, J. Org. Chem., 1996, 61, pp. 8310-8311.

* cited by examiner

*Primary Examiner* — T. Victor Oh
(74) *Attorney, Agent, or Firm* — Knobbe Martens Olson & Bear LLP

(57) ABSTRACT

To provide a method for producing an epoxy compound having fewer residual quaternary salt compound by removing the quaternary salt compound from an organic solution containing an epoxy compound and the quaternary salt compound.

A method for producing an epoxy compound comprising the following step 1, step 2, and step 3:

step 1: a step in which in a mixture liquid containing an olefin compound, an aqueous hydrogen peroxide solution, a quaternary salt compound, a heteropoly acid, and an organic solvent, the olefin compound is subjected to the oxidation reaction to obtain an organic solution (A) containing an epoxy compound, step 2: a step in which an aqueous inorganic alkali solution is allowed to contact with the organic solution (A) to obtain an organic solution (B) containing the epoxy compound, and step 3: a step in which an acidic aqueous solution containing a polymer having at least one functional group selected from the group consisting of a carboxyl group and a sulfonic acid group is allowed to contact with the organic solution (B) to obtain an organic solution (C) containing the epoxy compound.

13 Claims, No Drawings

METHOD FOR PRODUCING EPOXY COMPOUND

CROSS-REFERENCE TO RELATED APPLICATION

This application claims priority to Japanese Patent Application No. 2012-151133 filed on Jul. 5, 2012, and to Japanese Patent Application No. 2013-138260 filed on Jul. 1, 2012, and the disclosures of which including the specifications, the drawings, and the claims are hereby incorporated by reference in their entirety.

FIELD OF THE INVENTION

The present invention relates to a method for producing an epoxy compound with hydrogen peroxide and also relates to an epoxy compound obtained by the production method.

BACKGROUND OF THE INVENTION

In general, an epoxy compound are produced by subjecting an olefin compound to oxidation reaction in the presence of an organic peroxide such as peracetic acid or performic acid, but in this production method, there are problems such that the organic peroxide is corrosive, the oxidation reaction tends to be out of control, and an addition product of the organic peroxide as a byproduct remains in the resulting epoxy compound.

Therefore, a method for oxidizing an olefin compound with hydrogen peroxide in place of the organic peroxide has been studied. This production method is advantageous industrially because hydrogen peroxide as an oxidizing agent is not corrosive, the oxidation reaction is under control, and the byproduct is only water.

However, it is difficult to oxidize olefins with hydrogen peroxide only. Thus, for example, in JP-A-2004-115455, JP-A-2003-192679, Bull. Chem. Soc. Jpn., 70, 905-915 (1997), and J. Org. Chem., 61, 8310 (1996), a method of subjecting an olefin compound to oxidation reaction effectively in an organic solvent containing an aqueous hydrogen peroxide solution and a combination of a quaternary salt compound and a heteropoly acid is disclosed. However, a large amount of the quaternary salt compounds remain in the epoxy compound obtained by this production method.

Therefore, for example, a method where a chemically activated carbon is added to an organic solution containing an epoxy compound and a quaternary salt compound so that the quaternary salt compound is physically adsorbed on the activated carbon is disclosed in JP-A-2010-70480. However, since the activated carbon also adsorbs other substances in addition to the quaternary salt compound, its amount used is increased and this is not economical.

Meanwhile, the quaternary salt compound is also considered to be removed by various chemical adsorption means. Such means include, for example, use of an aqueous cyclodextrin solution as described in JP-A-2008-246287 and use of an ion exchange resin as described in JP-A-2007-181833.

However, both means are intended to remove a quaternary salt compound contained in an aqueous solution and are not suitable for removal of a quaternary salt compound contained in an organic solution. For example, when the aqueous cyclodextrin solution is added to an organic solvent solution containing an epoxy compound and a quaternary salt compound, an emulsion occurs, therefor it becomes difficult or impossible to remove the quaternary salt compound. Further, since an ion exchange resin is typically hydrophilic and difficult to be wet with an organic solution, it is actually difficult to adsorb the quaternary salt compound contained therein on such a resin.

PRIOR ART LITERATURE

Patent Document

[Patent document 1] JP-A No. 2004-115455
[Patent document 2] JP-A No. 2003-192679
[Patent document 3] JP-A No. 2010-70480
[Patent document 4] JP-A No. 2008-246287
[Patent document 5] JP-A No. 2007-181833

Non-Patent Document

[Non-Patent document 1] Bull. Chem. Soc. Jpn., 70, 905-915 (1997)
[Non-Patent document 2] J. Org. Chem., 61, 8310 (1996)

SUMMARY OF THE INVENTION

Technical Problem

An object of the present invention is to provide a method for producing an epoxy compound having fewer residual quaternary salt compound by removing the quaternary salt compound from an organic solution containing an epoxy compound and the quaternary salt compound.

Solution to Problem

As a result of investigation, the present inventors have found that the object described above can be achieved by subjecting an olefin compound to oxidation reaction in a mixture liquid containing an aqueous hydrogen peroxide solution, a quaternary salt compound, a heteropoly acid, and an organic solvent to obtain an organic solution containing an epoxy compound and further subjecting the organic solution to predetermined two steps.

The present invention relates to a method for producing an epoxy compound comprising the following step 1, step 2, and step 3 and also relates to an epoxy compound obtained by the production method.

A method for producing an epoxy compound comprising the following step 1, step 2, and step 3:

step 1: a step in which in a mixture liquid containing an olefin compound, an aqueous hydrogen peroxide solution, a quaternary salt compound, a heteropoly acid, and an organic solvent, the olefin compound is subjected to the oxidation reaction to obtain an organic solution (A) containing an epoxy compound, step 2: a step in which an aqueous inorganic alkali solution is allowed to contact with the organic solution (A) to obtain an organic solution (B) containing the epoxy compound, and step 3: a step in which an acidic aqueous solution containing a polymer having at least one functional group selected from the group consisting of a carboxyl group and a sulfonic acid group is allowed to contact with the organic solution (B) to obtain an organic solution (C) containing the epoxy compound.

Advantageous Effects of the Invention

Since the method for producing an epoxy compound according to the present invention includes the step 1 described above, it is possible to convert various olefin compounds, particularly cyclic olefin compounds that are difficult to be subjected to oxidation reaction due to their steric hindrance, into epoxy compounds safely and efficiently. Moreover, additional provision of the predetermined steps 2 and 3 after the step 1 makes it possible to finally obtain a high-purity epoxy compound with fewer residual quaternary salt compound.

The epoxy compound obtained by the production method of the present invention is useful as intermediates for pharmaceuticals and agrochemicals; raw materials for various perfumes and polymers; semiconductor materials and raw materials for electric/electronic materials; reactive diluents; sealants; detergents; polymer modifiers; ink components for photocurable inkjet; and raw materials for coating materials, adhesives, and resists.

DESCRIPTION OF EMBODIMENTS

The production method of the present invention is characterized by including the following step 1, step 2, and step 3.

step 1: a step in which in a mixture liquid containing an olefin compound, an aqueous hydrogen peroxide solution, a quaternary salt compound, a heteropoly acid, and an organic solvent, the olefin compound is subjected to the oxidation reaction to obtain an organic solution (A) containing an epoxy compound, step 2: a step in which an aqueous inorganic alkali solution is allowed to contact with the organic solution (A) to obtain an organic solution (B) containing the epoxy compound, and step 3: a step in which an acidic aqueous solution containing a polymer having at least one functional group selected from the group consisting of a carboxyl group and a sulfonic acid group is allowed to contact with the organic solution (B) to obtain an organic solution (C) containing the epoxy compound.

The step 1 is a step of oxidizing an olefin compound as a substrate to convert into an epoxy compound.

As the olefin compound, various known olefin compounds can be used without particular limitation as long as they are unsaturated hydrocarbons having at least one carbon-carbon double bond in the molecule. Further, the position of the carbon-carbon double bond in the olefin compound is not particularly limited, and such a double bond may be located at the molecular ends and/or within the molecule of the olefin compound.

Further, the olefin compound may have a variety of substituents. Examples of the substituent include hydrocarbon groups (e.g., alkyl group, alkenyl group, aryl group, and alkoxy group); polar groups (e.g., hydroxyl group, carboxyl group, mercapto group, amino group, amino group substituted with the hydrocarbon group, amide group, nitro group, cyano group, acyl group, ester group, ether group, epoxy group, and carbonyl group); heterocyclic structure-containing groups; halogen atoms; and the like. Hereinafter, the same shall apply to the "substituent".

Examples of the alkyl group include linear alkyl groups (e.g., methyl group, ethyl group, n-propyl group, n-butyl group, n-pentyl group, n-hexyl group, n-octyl group, n-nonyl group, and n-decyl group); branched alkyl groups (e.g., isopropyl group, isobutyl group, sec-butyl group, tert-butyl group, and isooctyl group); cycloalkyl groups (e.g., cyclobutyl group, cyclopentyl group, cyclohexyl group, cycloheptyl group, cyclooctyl group, cyclononyl group, cyclodecyl group, cyclododecyl group, and norbornyl group); and the like.

Examples of the alkenyl group include linear alkenyl groups (e.g., ethenyl group, n-butenyl group, n-propenyl group, n-pentenyl group, n-hexenyl group, n-octenyl group, n-nonenyl group, and n-decenyl group); branched alkenyl groups (e.g., isopropenyl group, isobutenyl group, sec-butenyl group, tert-butenyl group, and isooctenyl group); cycloalkenyl groups (e.g., cyclopentenyl group, cyclohexenyl group, cycloheptenyl group, cyclooctenyl group and norbornenyl group); and the like.

Examples of the aryl group include phenyl groups and naphthyl groups. In addition, the aryl group may have the substituent. Specific examples of the aryl group having the substituent include a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 2-methylphenyl group, a 4-methylphenyl group, a 4-methoxyphenyl group, a 4-acetylphenyl group, and the like.

The alkoxy groups include, in addition to alkoxy groups with about 1 to 10 carbon atoms (e.g., methoxy group, ethoxy group, propoxy group, butoxy group, t-butoxy group, cyclohexyloxy group, and pentyloxy group), phenoxy groups, benzyloxy groups, naphthyloxy groups, and the like.

Examples of the heterocyclic structure-containing group include groups derived from heterocyclic compounds such as aziridine, oxirane, thiirane, azirine, oxirene, thiirene, azetidine, oxetane, thietane, azete, azolidine, oxolane, thiolane, azole, oxol, thiol, azine, oxane, thiane, pyridine, pyrylium ions, thiopyrylium ions, azepane, oxepane, thiepane, azepine, oxepine, thiepine, imidazole, pyrazole, oxazole, thiazole, imidazoline, pyrazine, morpholine, thiazine, indole, isoindole, benzoimidazole, purine, quinoline, isoquinoline, quinoxaline, cinnoline, pteridine, and benzopyran.

Examples of the halogen atom include fluorine, chlorine, bromine, and iodine.

Among the olefin compounds, the production method of the present invention is suitable particularly for the epoxidation of (a) an olefin compound that is difficult to be subjected to oxidation reaction because of large steric hindrance around the carbon-carbon double bond that is a reactive site and (b) an olefin compound that is difficult to enhance its purity by known distillation purification means because of low volatility of the epoxy compound obtained, though the epoxidation itself of the carbon-carbon double bond that is a reactive site is easily performed. Examples of such an olefin compound include various cyclic olefin compounds and/or long-chain linear olefin compounds.

The cyclic olefin compounds include olefin compounds having at least one skeleton selected from the group consisting of the cycloalkyl group and the cycloalkenyl group in the molecule. Further, one or two or more of the substituents may be bonded to the cycloalkyl group and the cycloalkenyl group, and examples of such a substituent include hydrocarbon groups (e.g., alkyl group with about 1 to 5 carbon atoms and alkenyl group with about 2 to 5 carbon atoms) and polar groups (e.g., hydroxyl group and ester group).

Specific species of the cyclic olefin compound include an olefin compound represented by the following general formula (1), an olefin compound represented by the following general formula (2), an olefin compound represented by the following general formula (3), an olefin compound represented by the following general formula (4), an olefin compound represented by the following general formula (5), an olefin compound represented by the following general formula (6), and various known terpene-based olefin compounds. However, those corresponding to the terpene-based olefin compounds are excluded from the olefin compound represented by the general formula (4)

General formula (1)

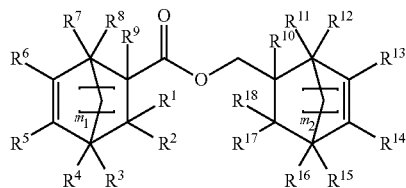

[Formula 1]

(wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$, each represent a hydrogen atom or the substituent. In addition, $m_1$ and $m_2$ each represent 0 or 1. Further, when $m_1$ is 1, this means that a methylene group is present in the crosslinked form in the ring, and when $m_1$ is 0, this means that a methylene group is not present in the ring. In addition, when $m_2$ is 1, this means that a methylene group is present in the crosslinked form in the ring, and when $m_2$ is 0, this means that a methylene group is not present in the ring. However, when $m_1$ is 1, only $R^3$ is bonded to the carbon atom to which $R^3$ and $R^4$ are bonded and only $R^7$ is bonded to the carbon atom to which $R^7$ and $R^8$ are bonded, and $R^3$ and $R^7$ each represent hydrogen or the substituent as described above. Further, when $m_2$ is 1, only $R^{11}$ is bonded to the carbon atom to which $R^{11}$ and $R^{12}$ are bonded and only $R^{15}$ is bonded to the carbon atom to which $R^{15}$ and $R^{16}$ are bonded, and $R^{11}$ and $R^{15}$ each represent hydrogen or the substituent as described above.)

General formula (2)

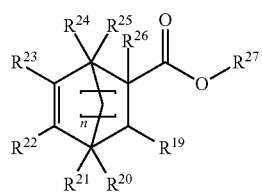

[Formula 2]

(wherein, $R^{19}$, $R^{20}$, $R^{21}$, $R^{22}$, $R^{23}$, $R^{24}$, $R^{25}$, $R^{26}$, and $R^{27}$, each represent a hydrogen atom or the substituent. In addition, n represents 0 or 1, and when n is 1, this means that a methylene group is present in the crosslinked form in the ring, and when n is 0, this means that a methylene group is not present in the ring. However, when n is 1, only $R^{20}$ is bonded to the carbon atom to which $R^{20}$ and $R^{21}$ are bonded and only $R^{24}$ is bonded to the carbon atom to which $R^{24}$ and $R^{25}$ are bonded, and $R^{20}$ and $R^{24}$ each represent hydrogen or the substituent as described above.)

General formula (3)

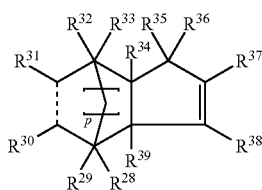

[Formula 3]

(wherein, $R^{28}$, $R^{29}$, $R^{30}$, $R^{31}$, $R^{32}$, $R^{33}$, $R^{34}$, $R^{35}$, $R^{36}$, $R^{37}$, $R^{38}$, and $R^{39}$, each represent a hydrogen atom or the substituent. In addition, p represents 0 or 1, and when p is 1, this means that a methylene group is present in the crosslinked form in the ring, and when p is 0, only $R^{28}$ is bonded to the carbon atom to which $R^{28}$ and $R^{29}$ are bonded and only $R^{32}$ is bonded to the carbon atom to which $R^{32}$ and $R^{33}$ are bonded, and $R^{28}$ and $R^{32}$ each represent hydrogen or the substituent as described above. Further, the dashed line represents a carbon-carbon single bond or a carbon-carbon double bond.)

General formula (4)

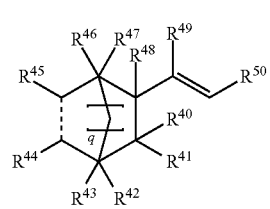

[Formula 4]

(wherein, $R^{40}$, $R^{41}$, $R^{42}$, $R^{43}$, $R^{44}$, $R^{45}$, $R^{46}$, $R^{47}$, $R^{48}$, $R^{49}$, and $R^{50}$, each represent a hydrogen atom or the substituent. In addition, q represents 0 or 1, and when q is 1, this means that a methylene group is present in the crosslinked form in the ring, and when q is 0, this means that a methylene group is not present in the ring. However, when q is 1, only $R^{42}$ is bonded to the carbon atom to which $R^{42}$ and $R^{43}$ are bonded and only $R^{46}$ is bonded to the carbon atom to which $R^{46}$ and $R^{47}$ are bonded, and $R^{42}$ and $R^{46}$ each represent hydrogen or the substituent as described above. Further, the dashed line represents a carbon-carbon single bond or a carbon-carbon double bond.)

General formula (5)

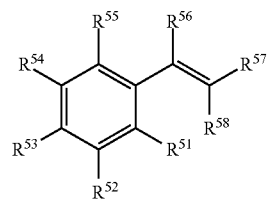

[Formula 5]

(wherein, $R^{51}$, $R^{52}$, $R^{53}$, $R^{54}$, $R^{55}$, $R^{56}$, $R^{57}$ and $R^{58}$ each represent a hydrogen atom or the substituent.)

General formula (6)

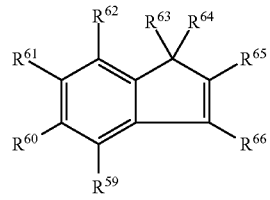

[Formula 6]

(wherein, $R^{59}$, $R^{60}$, $R^{61}$, $R^{62}$, $R^{63}$, $R^{64}$, $R^{65}$ and $R^{66}$ each represent a hydrogen atom or the substituent.)

Specific examples of the "substituent" in the general formulas (1), (2), (3), (4), (5), and (6) include preferably alkyl groups with about 1 to 5 carbon atoms among the alkyl groups described above, the polar groups (e.g., halogen and hydroxyl group), and the like.

The terpene-based olefin compound refers to a hydrocarbon compound represented by $(C_5H_8)_r$ (r is an integer), a derivative derived from the hydrocarbon, and a compound having a different number of double bonds and a different unsaturation degree from the foregoing. Specific examples thereof include oligomers (e.g., terpene hydrocarbon, terpene alcohol, terpene aldehyde, terpene ketone, terpene dimer, terpene trimer, and terpene tetramer), other compounds, and the like. Examples of the terpene hydrocarbon include monoterpenes (e.g., α-pinene, β-pinene, limonene, α-phellandrene, β-phellandrene, α-terpinene, γ-terpinene, o-cimene, myrcene, camphene, terpinolene, sylvestrene, sabinene, carene, tricyclene, and fenchene); sesquiterpenes (e.g., longifolene, caryophyllene, isocaryophyllene, aromadendrene, bisabolene, santalene, zingiberene, curcumene, cadinene, sesquibenihene, and cedrene); diterpenes (e.g., campholene, podocarprene, mirene, phyllocladene, and totalene); and the like. The terpene derivatives include 1-carvone, sobrerole, geraniol, geranyl acetate, citronellyl acetate, terpinyl acetate, citral, citronellal, citronellol, dihydromyrcenol, and linalool, and other compounds obtained by the reaction of the terpene hydrocarbon as a raw material, and the like. In addition, the terpene-based olefin compounds include optical isomers. Examples of the optical isomer of the α-pinene include (1R)-(+)-α-pinene and (1S)-(−)-α-pinene. In case of the limonene, the optical isomers include (l)-limonene and (d)-limonene. Further, the limonene derivatives include limonene-1,2-oxide.

Examples of the long-chain linear olefin compound include compounds represented by the following general formula (7) (provided that the compounds represented by the general formulas (1), (2), (3), (4), (5), and (6), and compounds corresponding to the terpene-based olefin compounds are excluded).

General formula (7)

[Formula 7]

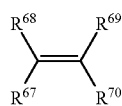

(wherein, $R^{67}$, $R^{68}$, $R^{69}$, and $R^{70}$ each represent a hydrogen atom or an alkyl group with about 3 to 30 carbon atoms, preferably about 6 to 30 carbon atoms (provided that a cycloalkyl group is excluded) or an alkenyl group with about 3 to 30 carbon atoms, preferably about 6 to 30 carbon atoms (provided that a cycloalkenyl group is excluded) with the proviso that the case where $R^7$, $R^{68}$, $R^{69}$, and $R^{70}$ are all hydrogen is excluded. The number of carbon-carbon double bond(s) contained in the alkenyl group is about 1 to 3. In addition, the alkyl group and the alkenyl group may have the substituent (s) as described above.)

Specific examples of the compound represented by the general formula (7) include linear α-olefins with about 6 to 30 carbon atoms (e.g., 1-hexene, 1-heptene, 1-octene, 1-nonene, 1-decene, 1-dodecene, 1-tetradecene, 1-pentadecene, 1-hexadecene, 1-octadecene, 1-eicocene, 1-docoscene, 1-tetracocene, 1-octacocene, and 1-triacontene), branched α-olefins (e.g., 2,4,4-trimethyl-1-pentene.), corresponding internal olefins thereof, and the like. Further, the linear α-olefins and the internal olefins may have the substituent (s) as mentioned above.

The olefin compound used in the present invention may be a pure product or a mixture of plural olefin compounds, or may be a mixture of geometrical isomers and optical isomers.

The aqueous hydrogen peroxide solution acts as an oxidizing agent for olefin compounds. The concentration thereof is not particularly limited, but it is usually about 0.1 to 100% by weight, preferably about 1 to 80% by weight, and further preferably about 10 to 60% by weight.

The amount used of the aqueous hydrogen peroxide solution is not particularly limited, but hydrogen peroxide is usually used within a range of about 0.001 to 10 equivalents, preferably about 0.01 to 5 equivalents, and more preferably about 0.1 to 2 equivalents, per one carbon-carbon double bond contained in the olefin compound. In the case where the olefin compound has two or more carbon-carbon double bonds, an epoxy compound in which the resulting carbon-carbon double bond remains can be obtained by appropriately changing the amount used of the aqueous hydrogen peroxide solution.

Various known compounds can be used as the quaternary salt compound without any particular limitation, and in particular, quaternary cationic species represented by the following general formula (8) is preferable.

General formula (8)

[Formula 8]

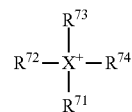

(wherein, $R^{71}$, $R^{72}$, $R^{73}$, and $R^{74}$ may be the same or different, and each represent the alkyl group, alkenyl group, or phenyl group as described above. In addition, the alkyl or alkenyl group may be bonded to the phenyl group. Further, X represents a nitrogen atom or a phosphorus atom.)

The number of the carbon atoms of the alkyl or alkenyl group constituting $R^{71}$, $R^{72}$, $R^{73}$, and $R^{74}$, respectively is not particularly limited, and is usually about 6 to 20.

In addition, examples of anionic species that forms a pair with the quaternary cationic species include chloride ions, bromide ions, iodide ions, hydroxide ions, nitrate ions, sulfate ions, hydrogen sulfate ions, acetate ions, carbonate ions, hydrogen carbonate ions, phosphate ions, hydrogenphosphate ions, and the like.

Examples of the quaternary salt compound in which X is a nitrogen atom include a trioctylmethyl ammonium salt, a trioctylethyl ammonium salt, a tridecanylmethyl ammonium salt, a trialkylmethyl (mixed type of octyl group and decanyl group) ammonium salt, a trihexadecylmethyl ammonium salt, a dialkyldimethyl (mixed type of C8 to C18 alkyl chains) ammonium salt, a dilauryldimethyl ammonium salt, a didecyldimethyl ammonium salt, a dioctyldimethyl ammonium salt, a dioleyldimethyl ammonium salt, a lauryltrimethyl ammonium salt, a stearyltrimethyl ammonium salt, a lauryldimethylbenzyl ammonium salt, a distearyldimethyl ammonium salt, a tetrabutyl ammonium salt, a benzyltrimethyl ammonium salt, a benzyltriethyl ammonium salt, a benzyltributyl ammonium salt, a tetrapentyl ammonium salt, a tetrabutylammonium salt, a tetramethylammonium salt, and the like, and these salts can be used alone or in combination of two or more kinds thereof. Further, the "dialkyldimethyl (mixed type of C8 to C18 alkyl chains) ammonium salt" refers specifically to an ammonium salt in which the alkyl group is derived from coconut oil (the same shall apply hereinafter), and, examples thereof include ARQUAD 2C-75 (trade name) manufactured by Lion Corporation.

Examples of the quaternary salt compound in which X is a phosphorus atom include tetraphenyl phosphonium, tetra-n-ethyl phosphonium, tetra-n-propyl phosphonium, tetra-n-butyl phosphonium, di-n-decyldimethyl phosphonium, di-n-octadecyldimethyl phosphonium, tri-n-decylmethyl phosphonium, benzyltributyl phosphonium, phenyltrimethyl phosphonium, tetraphenyl phosphonium, and the like, and these phosphoniums may be used alone or in combination of two or more kinds thereof.

As the quaternary salt compound, a quaternary ammonium salt compound having at least one alkyl group with about 6 to 20 carbon atoms in the molecule, particularly a quaternary ammonium salt compound having 2 to 3 such alkyl groups is preferable from the viewpoint of restraining an ammonium salt compound from remaining in the target epoxy compound. Specific examples of the quaternary ammonium salt compound include preferably the trioctylmethyl ammonium salt, the trialkylmethyl (mixed type of octyl group and decanyl group) ammonium salt, the dialkyldimethyl (mixed type of C8 to C18 alkyl chains) ammonium salt, the dilauryldimethyl ammonium salt, the didecyldimethyl ammonium salt, the dioctyldimethyl ammonium salt, and the like, and these ammonium salts may be used alone or in combination of two or more kinds thereof. In addition, as the anionic species that forms each ammonium salt, one or two or more kinds of anionic species selected from chloride ions, carbonate ions, acetate ions, hydrogen sulfite ions, and the like are preferable.

The amount used of the quaternary salt compound is not particularly limited, but the quaternary salt compound is usually used in an amount of about 0.0001 to 20 moles, preferably about 0.001 to 15 moles, and more preferably about 0.01 to 10 moles, per 100 moles of the olefin compound.

In the production method of the present invention, the heteropoly acid is a compound that acts as an oxidizing agent for olefins together with the aqueous hydrogen peroxide solution, and is obtained by introducing a hetero atom into various known isopoly acids or metal salts thereof.

The isopoly acids include inorganic acids mainly composed of inorganic elements (e.g., tungsten, molybdenum, chromium, manganese, vanadium, niobium, rhenium, iron, ruthenium, cobalt, nickel, palladium, platinum, copper, silver, gold, tin, titanium, zirconium, rhodium, iridium, osmium, and zinc) and salts thereof.

In addition, the hetero atoms include oxygen, sulfur, phosphorus, ammonium, potassium, sodium, and the like.

As the heteropoly acid, a tungsten-based heteropoly acid obtained by introducing phosphorus into a tungsten-containing isopoly acid and a molybdenum-based heteropoly acid obtained by introducing phosphorus into a molybdenum-containing isopoly acid are preferable from the point that epoxidation of the olefin compound, particularly the cyclic olefin compound, is easily achieved.

The tungsten-based heteropoly acids include tungstic acid, tungsten trioxide, tungsten trisulfide, tungsten phosphate, ammonium tungstate, potassium tungstate (dihydrate), 12-phosphotungstic acid (hydrate), and sodium tungstate (dihydrate). Of these, tungstic acid, tungsten trioxide, tungsten phosphate, and sodium tungstate (dihydrate) are preferable, and in particular, tungstic acid, 12-phosphotungstic acid (hydrate), sodium tungstate (dihydrate), and phosphotungstic acid are preferable. These acids may be used alone or in combination of two or more kinds thereof.

The molybdenum-based heteropoly acids include molybdic acid and phosphomolybdic acid. Further, these may be hydrates.

As the heteropoly acid in the present invention, it is also possible to use the reaction product of a hetero atom donor with isopoly acid or a salt thereof, in addition to commercially available products as they are. In addition, examples of the hetero atom donor include phosphoric acids such as phosphoric acids, phosphonic acids, and salts thereof.

Examples of the phosphoric acids include phosphoric acid, polyphosphoric acid, pyrophosphoric acid, hexametaphosphoric acid, hypophosphorous acid, phosphorous acid, dodecylphosphoric acid, 2-ethylhexylphosphoric acid, and the like; and examples of the phosphoric acid salts include sodium phosphate, potassium phosphate, ammonium phosphate, sodium dihydrogen phosphate, disodium hydrogen phosphate, potassium hydrogen phosphate, ammonium hydrogen phosphate, sodium polyphosphate, sodium hexametaphosphate, acidic sodium hexametaphosphate, sodium pyrophosphate, disodium dihydrogen pyrophosphate, sodium hypophosphite, sodium phosphite, and the like. Further, examples of the phosphonic acids include methylphosphonic acid, ethylphosphonic acid, n-propylphosphonic acid, isopropylphosphonic acid, n-butylphosphonic acid, t-butylphosphonic acid, phenylphosphonic acid, 4-methoxyphenylphosphonic acid, 4-aminophenylphosphonic acid, 1-hydroxyethane-1,1-bis(phosphonic acid), nitrilotris (methylenephosphonic acid), and the like. Moreover, examples of the salts of the phosphonic acids include sodium phenylphosphonate and the like. Among these, phosphoric acid, phenylphosphonic acid, phosphorous acid, hypophosphorous acid, 2-ethylhexylphosphoric acid, lauryl phosphate, sodium dihydrogen phosphate, and the like are preferable.

The amount used of the heteropoly acid is not particularly limited, but it is usually about 0.0001 to 20 moles, preferably about 0.001 to 15 moles, and more preferably about 0.01 to 10 moles, per 100 moles of the olefin compound. If the olefin compound has two or more carbon-carbon double bonds, it is also possible to obtain an epoxy compound in which the resulting carbon-carbon double bond remains by appropriately changing the amount used of the heteropoly acid.

Further, when the reaction product of the hetero atom donor with the isopoly acid or a salt thereof is used as the heteropoly acid, the amount used of the isopoly acid is about 0.0001 to moles, preferably about 0.001 to 15 moles, and more preferably about 0.01 to 10 moles, per 100 moles of the olefin compound. In addition, the amount used of the hetero atom donor (e.g., phosphoric acids) is about 0.0001 to 10 moles, preferably about 0.001 to 15 moles, and more preferably about 0.01 to 10 moles, based on the olefin compound.

The organic solvent is not particularly limited as long as it is sparingly soluble or insoluble in water and acts as a solvent for liquid-liquid extraction. Specific examples thereof include aromatic hydrocarbon-based organic solvents (e.g., toluene and xylene); chlorinated organic solvents (e.g., chloroform, chlorobenzene, o-dichlorobenzene, dichlorotoluene, dichloromethane, and dichloroethane); alicyclic organic solvents (e.g., hexane and cyclohexane); ester-based organic solvents (e.g., ethylacetate and butyl acetate); and ether-based organic solvents (e.g., diethyl ether). Of these, when the aromatic hydrocarbon-based organic solvent, in particular toluene, is used, the quaternary salt compound is hard to remain in the resulting epoxy compound. The amount used of the organic solvent is not particularly limited, and may be appropriately set.

In the step 1, after subjecting the olefin compound to oxidation reaction in a mixture liquid containing the olefin compound, aqueous hydrogen peroxide solution, quaternary salt compound, heteropoly acid, and organic solvent, the resulting solution is separated into an aqueous phase and an organic phase. Then, this organic phase is regarded as an organic solution (A) containing the epoxy compound.

The order of the addition of the olefin compound, aqueous hydrogen peroxide solution, quaternary salt compound, heteropoly acid, and organic solvent to the reaction system in the step 1 is not particularly limited. There are exemplified a method where all the components are charged into a suitable reaction vessel at a time and a method where an aqueous catalyst solution containing the aqueous hydrogen peroxide solution, quaternary salt compound, and heteropoly acid is prepared once, and then an organic solution containing the olefin compound and organic solvent is added to the catalyst solution, followed by stirring and mixing the entire reaction system. The quaternary salt compound acts as a phase transfer catalyst. The isopoly acid and the hetero atom donor (e.g., phosphoric acids) may be used independently in place of the heteropoly acid, and, in this case, a heteropoly acid is produced in the reaction system.

In addition, the reaction system is a two-phase mixture system, and phase separation between the organic phase and the aqueous phase occurs by leaving the reaction system as it is. At this time, the pH of the aqueous phase is usually about 0.1 to 7, preferably about 0.5 to 4.0 from the viewpoint of improving the rate of the epoxidation reaction or suppressing the formation of byproducts. Examples of the pH adjusting means include acids (e.g., sulfuric acid), acidic salts (e.g., phosphate), alkali metal hydroxides (e.g., sodium hydroxide), and the like. Then, after the completion of the oxidation reaction, an organic solution (A) is obtained by removing the aqueous phase of the aqueous and organic phases or collecting the organic phase.

The conditions in the oxidation reaction in the step 1 are not particularly limited. Usually, the reaction temperature is about −30° C. to 140° C., preferably about 0° C. to 80° C., and more preferably about 20° C. to 60° C. Further, the reaction time is usually about 30 minutes to 24 hours, preferably about 1 to 20 hours, and more preferably about 2 to 12 hours. In addition, the pressure during the reaction is usually about 80 kPa to 1 MPa.

In the step 1 of the present invention, various known neutral inorganic salts may be present in the mixture liquid, which is the oxidation reaction system of the olefin compound. The use of the neutral inorganic salt makes it possible to prevent isomerization or degradation of an epoxy compound particularly unstable to acids and heat among the epoxy compounds derived from the olefin compound. Examples of the epoxy compound include the epoxy compound obtained from the olefin compound represented by the general formula (4) and the epoxy compound obtained from the terpene-based compound. The neutral inorganic salt is preferably sulfates and examples of the sulfates include lithium sulfate, sodium sulfate, potassium sulfate, calcium sulfate, magnesium sulfate, and the like. The amount used of the neutral inorganic salt is not particularly limited, but it is usually about 1 to 500 moles, preferably about 5 to 250 moles, and more preferably about 10 to 100 moles, per 100 moles of the olefin compound.

Further, after the completion of the step 1, for example, an aqueous solution of sodium thiosulfate or the like as a substance for decomposing hydrogen peroxide remaining in the organic solution (A) may be added to the organic solution (A) before the step 2. Also, the epoxy compound contained in the organic solution (A) may be once isolated by known purification means such as distillation, and a solution obtained by dissolving the isolated product again in the organic solvent can be regarded as the organic solution (A).

The step 2 is a step to obtain an organic solution (B) containing the epoxy compound after contacting an aqueous inorganic alkali solution with the organic solution (A). Specifically, after mixing the organic solution (A) with various known aqueous inorganic alkali solution, the resulting solution is separated into an aqueous phase and an organic phase. Then, an organic solution (B) containing the epoxy compound is obtained by removing the aqueous phase or collecting the organic phase. This step is a so-called a washing step, and, as a result of transfer of water-soluble substances such as heteropoly acids contained in the organic solution (A) to the aqueous inorganic alkali solution, the concentration of the epoxy compound in the resulting organic solution (B) is increased.

Examples of the aqueous inorganic alkali solution include aqueous solutions of sodium hydroxide, potassium hydroxide, lithium hydroxide, calcium hydroxide, ammonium hydroxide, tetramethyl ammonium hydroxide, sodium phosphate, potassium phosphate, lithium phosphate, calcium phosphate, sodium carbonate, potassium carbonate, lithium carbonate, calcium carbonate, sodium hydrogen carbonate, sodium acetate, potassium acetate, lithium acetate, calcium acetate, and the like. Further, the amount used of the inorganic alkali solution is not particularly limited, but the inorganic alkali content may be usually in a range of about 0.1- to 100-fold moles, preferably about 0.5- to 50-fold moles, per 100 moles of the heteropoly acid used. In addition, the concentration of the aqueous inorganic alkali solution is not also particularly limited, but it is usually about 0.001 to 50%, preferably about 0.01 to 10%.

The step 3 is a step of obtaining an organic solution (C) containing the epoxy compound after contacting the organic solution (B) obtained in the step (2) with an acidic aqueous solution containing a polymer having at least one functional group selected from the group consisting of a carboxyl group and a sulfonic acid group (hereinafter may be simply referred to as polymer) (hereinafter may be simply referred to as aqueous polymer solution). Specifically, after mixing the organic solution (B) with the aqueous polymer solution, the resulting solution is separated into an aqueous phase and an organic phase. Then, an organic solution (C) containing the epoxy compound is obtained by removing the aqueous phase or collecting the organic phase. In this step, the contact of the polymer with the quaternary salt compound contained in the organic solution (B) allows an insoluble salt obtained by adsorption of the quaternary salt compound onto the polymer to precipitate in the organic phase. In addition, some quaternary salt compounds are considered to transfer to the aqueous polymer solution, which is the aqueous phase. Then, the quaternary salt compound is removed from the organic solution (B) by filtering off the insoluble salt or separating the aqueous phase.

Examples of the polymer include polymers having a carboxyl group (e.g., poly(meth)acrylic acid, polymaleic acid, carboxymethyl cellulose, polyaspartic acid, polyglutamic acid, polyalginic acid, and poly(meth)acrylic acid/maleic acid copolymers); polymers having a sulfo group (e.g., polystyrene sulfonic acid); copolymers having both a carboxyl group and a sulfo group (e.g., poly(meth)acrylic acid/sulfonic acid copolymers); and metal salts thereof, among which polyacrylic acid, polymaleic acid, polystyrene maleic acid, polystyrene sulfonic acid, carboxymethyl cellulose, and alkali metal salts thereof are particularly preferable, and polyacrylic acid, polymaleic acid, and alkali metal salts thereof are especially preferable. The metals that form a salt include alkali metals (e.g., sodium and potassium); and alkaline earth metals (e.g., calcium and magnesium), among which sodium is particularly preferable. Further, the neutralization ratio of the polymer is not particularly limited, but it is usually about 10 to 90%.

In addition, the aqueous polymer solution needs to be acidic from the viewpoint of the removal efficiency of the quaternary salt compound contained in the organic solution (B), and the pH is usually about 1 to 6, preferably about 2 to 5. The adjustment of pH can be performed with the use of acids (e.g., sulfuric acid and hydrochloric acid) or alkalis (e.g., sodium hydroxide).

Also, the physical properties of the polymer are not particularly limited, but from the viewpoint of the removal efficiency of the quaternary salt compound contained in the organic solution (B), the weight average molecular weight (in terms of polystyrene as measured by gel permeation chromatography method. The same shall apply hereinafter.) is usually about 500 to 200,000, preferably about 1,000 to 100,000, and more preferably 1,500 to 55,000.

The concentration of the aqueous polymer solution is not particularly limited, but it is usually about 1 to 20% by weight from the viewpoint of the removal efficiency of the quaternary salt compound contained in the organic solution (B).

The amount used of the aqueous polymer solution is not particularly limited, but from the viewpoint of the removal efficiency of the quaternary salt compound contained in the organic solution (B), it is usually 0.5- to 5.0-fold weight, preferably 1- to 2.5-fold weight, based on the weight of the quaternary salt compound used in the preparation of the organic solution (A).

The temperature at the time of contacting the aqueous polymer solution with the organic solution (B), specifically the temperature of the mixture liquid of the two solutions, is not particularly limited, but it is usually about 0 to 100° C., preferably about 20 to 60° C., from the viewpoint of the removal efficiency of the quaternary salt compound contained in the organic solution (B), liquid-liquid extraction properties, workability, or the like. In addition, the contact time is not also particularly limited, but it is usually about 1 to 180 minutes, preferably about 5 to 60 minutes, from the viewpoint of the removal efficiency of the quaternary salt compound.

The amount of the quaternary salt compound contained in the organic solution (C) thus obtained is greatly reduced in comparison with that contained in the organic solution (A). Further, the epoxy compound obtained from the organic solution (C) has a high purity because the residual content of the quaternary salt compound contained therein is small.

The purity of the epoxy compound contained in the organic solution (C) can be quantified by known means such as gas chromatography. The amount of the quaternary salt compound contained in the organic solution (C) can also be quantified by a trace nitrogen analyzer. At this time, it is possible to use a calibration curve prepared for the same quaternary salt compound.

Further, the organic solution (C) can be further subjected to known purification means as needed, using an adsorbent such as activated carbon or silica, so that the epoxy compound having a further improved purity can be obtained.

The epoxy compound obtained by the production method of the present invention is a compound in which the carbon-carbon double bond contained in the olefin compound is converted to a 1,2-epoxyethane structure. Also, for example, in the case where an olefin compound containing two carbon-carbon double bonds is used as the starting material, the resulting epoxy compound may be a mixture of a monoepoxy body and a diepoxy body. However, the adjustment of the amount used of the oxidizing agent (aqueous hydrogen peroxide solution, heteropoly acid) also makes it possible to selectively obtain the diepoxy body in a large amount.

For example, a diepoxy compound represented by the following general formula (1') can be obtained from the olefin compound represented by the general formula (1).

General formula (1')

[Formula 9]

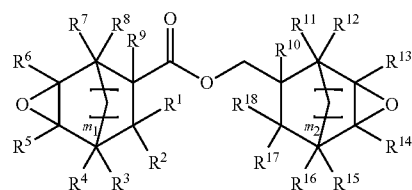

(wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$, each represent a hydrogen atom or the substituent. In addition, $m_1$ and $m_2$ each represent 0 or 1. Further, when $m_1$ is 1, this means that a methylene group is present in the crosslinked form in the ring, and when $m_1$ is 0, this means that a methylene group is not present in the ring. In addition, when $m_2$ is 1, this means that a methylene group is present in the crosslinked form in the ring, and when $m_2$ is 0, this means that a methylene group is not present in the ring. However, when $m_1$ is 1, only $R^3$ is bonded to the carbon atom to which $R^3$ and $R^4$ are bonded and only $R^7$ is bonded to the carbon atom to which $R^7$ and $R^8$ are bonded, and $R^3$ and $R^7$ each represent hydrogen or the substituent as described above. Further, when $m_2$ is 1, only $R^{11}$ is bonded to the carbon atom to which $R^{11}$ and $R^{12}$ are bonded and only $R^{15}$ is bonded to the carbon atom to which $R^{15}$ and $R^{16}$ are bonded, and $R^{11}$ and $R^{15}$ each represent hydrogen or the substituent as described above.)

In addition, an epoxy compound represented by the following general formula (2') can be obtained from the olefin compound represented by the general formula (2).

General formula (2')

[Formula 10]

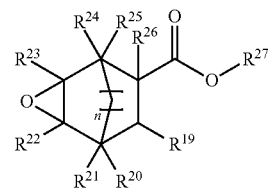

(wherein, $R^{19}$, $R^{20}$, $R^{21}$, $R^{22}$, $R^{23}$, $R^{24}$, $R^{25}$, $R^{26}$, and $R^{27}$, each represent a hydrogen atom or the substituent. In addition, n represents 0 or 1, and when n is 1, this means that a methylene group is present in the crosslinked form in the ring, and when n is 0, this means that a methylene group is not present in the ring. However, when n is 1, only $R^{20}$ is bonded to the carbon atom to which $R^2$ and $R^{21}$ are bonded and only $R^{24}$ is bonded to the carbon atom to which $R^{24}$ and $R^{25}$ are bonded, and $R^{20}$ and $R^{24}$ each represent hydrogen or the substituent as described above.)

In addition, a diepoxy compound represented by the following general formula (3') and a monoepoxy compound represented by the following general formula (3") can be obtained from the olefin compound represented by the general formula (3).

General formula (3')

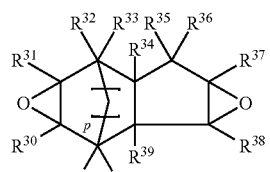

[Formula 11]

General formula (3'')

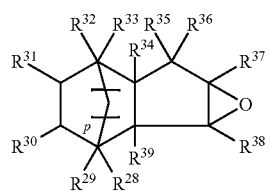

[Formula 12]

(wherein, $R^{28}$, $R^{29}$, $R^{30}$, $R^{31}$, $R^{32}$, $R^{33}$, $R^{34}$, $R^{35}$, $R^{36}$, $R^{37}$, $R^{38}$, and $R^{39}$, each represent a hydrogen atom or the substituent. In addition, p represents 0 or 1, and when p is 1, this means that a methylene group is present in the crosslinked form in the ring, and when p is 0, only $R^{28}$ is bonded to the carbon atom to which $R^{28}$ and $R^{29}$ are bonded and only $R^{32}$ is bonded to the carbon atom to which $R^{32}$ and $R^{33}$ are bonded, and $R^{28}$ and $R^{32}$ each represent hydrogen or the substituent as described above.)

In addition, an epoxy compound represented by the following general formula (4') and a monoepoxy compound represented by the following general formula (4") can be obtained from the olefin compound represented by the general formula (4).

General formula (4')

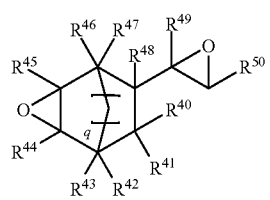

[Formula 13]

General formula (4")

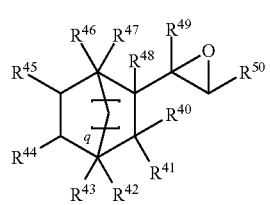

[Formula 14]

(wherein, $R^{40}$, $R^{41}$, $R^{42}$, $R^{43}$, $R^{44}$, $R^{45}$, $R^{46}$, $R^{47}$, $R^{48}$, $R^{49}$, and $R^{50}$, each represent a hydrogen atom or the substituent. In addition, q represents 0 or 1, and when q is 1, this means that a methylene group is present in the crosslinked form in the ring, and when q is 0, this means that a methylene group is not present in the ring. However, when q is 1, only $R^{42}$ is bonded to the carbon atom to which $R^{42}$ and $R^{43}$ are bonded and only $R^{46}$ is bonded to the carbon atom to which $R^{46}$ and $R^{47}$ are bonded and $R^{42}$ and $R^{46}$ each represent hydrogen or the substituent as described above.

In addition, an epoxy compound represented by the following general formula (5') can be obtained from the olefin compound represented by the general formula (5).

General formula (5')

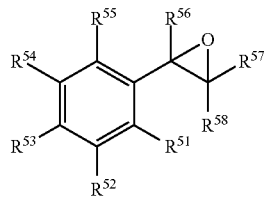

[Formula 15]

(wherein, $R^{51}$, $R^{52}$, $R^{53}$, $R^{54}$, $R^{55}$, $R^{56}$, $R^{57}$ and $R^{58}$ each represent a hydrogen atom or the substituent.)

In addition, an epoxy compound represented by the following general formula (6') can be obtained from the olefin compound represented by the general formula (6).

General formula (6')

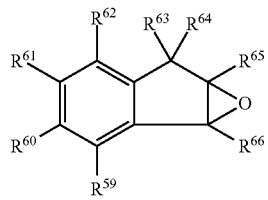

[Formula 16]

(wherein, $R^{59}$, $R^{60}$, $R^{61}$, $R^{62}$, $R^{63}$, $R^{64}$, $R^{65}$ and $R^{66}$ each represent a hydrogen atom or the substituent.)

Specific examples of the "substituent" in the general formulas (1'), (2'), (3'), (4'), (5'), and (6') include preferably alkyl groups with about 1 to 5 carbon atoms among the alkyl groups described above, the polar groups (e.g., halogen and hydroxyl group), and the like.

In addition, an epoxy compound in which the carbon-carbon double bond is converted to a 1,2-epoxyethane structure can be obtained from the terpene-based olefin compound (see WO 2011/010614).

In addition, an epoxy compound represented by the following general formula (7') can be obtained from the olefin compound represented by the general formula (7).

General formula (7')

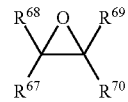

[Formula 17]

(wherein, $R^{67}$, $R^{68}$, $R^{69}$, and $R^{70}$ and represent a hydrogen atom or an alkyl group with about 3 to 30 carbon atoms, preferably about 6 to 30 carbon atoms (provided that a cycloalkyl group is excluded) or an alkenyl group with about 3 to 30 carbon atoms, preferably about 6 to 30 carbon atoms (provided that a cycloalkenyl group is excluded) with the proviso that the case where $R^{67}$, $R^{68}$, $R^{69}$, and $R^{70}$ are all hydrogen is excluded. The number of carbon-carbon double bond(s) contained in the alkenyl group is about 1 to 3. In addition, the alkyl group and the alkenyl group may have the substituent(s) as described above.)

EXAMPLE

The present invention will be described below in more detail by way of examples and comparative examples, but the invention is not intended to be limited thereto.

In each example, the term "purity" is a value (%) obtained by determining the peak intensity (detection voltage) of the epoxy compound contained in the organic solution (C) and the total intensity (detection voltage) of all peaks from the chart of the organic solution (C) as measured under the following conditions using a commercially available gas chromatography/mass spectrometer (product name "789OA/5975C", manufactured by Agilent Technologies Japan Ltd.); dividing the former by the latter; and multiplying the divided value by 100.
(Conditions)
 Column: HP-5MS (manufactured by Agilent) 30 m-0.25 mm-0.25 μm
 Injection volume: 1 μl, split ratio 50:1
 Injection temperature: 300° C.
 Detection temperature: 300° C.
 Oven: 50° C. (5 minutes, retention)–10° C./minute–300° C. (5 minutes, retention)
 Detector: Hydrogen flame ionization detector
 Measurement sample: A sample (0.1 mL) taken from the organic solution (C) and diluted with 2 mL of toluene.

In each example, the "removal rate (%) of the quaternary salt compound" refers to a value obtained from the expression: [1−[(residual amount (ppm) of quaternary salt compound contained in organic solution (C)/residual amount (ppm) of quaternary salt compound contained in organic solution (A))]×100]. The residual amount of the quaternary salt compound contained in the organic solution (A) or (C) is a value obtained by measurement using a commercially available trace nitrogen analyzer (product name "TN-10", manufactured by Mitsubishi Chemical Corporation), followed by determination based on a predetermined calibration curve. The calibration curve (vertical axis: nitrogen content; horizontal axis: emission intensity) has been prepared from a toluene solution containing only the quaternary salt compound as a solute.
(Conditions)
 Injection volume: 10 μl
 Measuring range: 50 ppm or 1 ppm Further, aqueous polymer solutions P1 to P16 used in the step 3 are as follows. Each amount used of the aqueous polymer solutions P1 to P16 is 2.5-fold weight of the polymer, based on the weight of the quaternary salt compound used in the step 1.

P1: An aqueous solution obtained by further adjusting a 5% dilute aqueous solution of a commercially available aqueous polyacrylic acid solution (molecular weight 6,000, manufactured by Toagosei Co., Ltd., trade name "Aron A-10SL") to pH 3 with sulfuric acid.

P2: An aqueous solution obtained by further adjusting a 5% dilute aqueous solution of Aron A-10SL to pH 4 with sulfuric acid.

P3: An aqueous solution obtained by further adjusting a 5% dilute aqueous solution of Aron A-10SL to pH 12 with sodium hydroxide.

P4: An aqueous solution obtained by further adjusting a 5% dilute aqueous solution of Aron A-10SL to pH 13 with sodium hydroxide.

P5: An aqueous solution obtained by further adjusting a 5% dilute aqueous solution of a commercially available aqueous polyacrylic acid/polystyrene sulfonic acid copolymer solution (molecular weight 6,000, manufactured by NIPPON SHOKUBAI CO., LTD., trade name "Aqualic GL366") to pH 2 with sulfuric acid.

P6: An aqueous solution obtained by further adjusting a 5% dilute aqueous solution of Aqualic GL366 to pH 3 with sulfuric acid.

P7: An aqueous solution obtained by further adjusting a 5% dilute aqueous solution of Aqualic GL366 to pH 4 with sulfuric acid.

P8: An aqueous solution obtained by further adjusting a 5% dilute aqueous solution of Aqualic GL366 to pH 12 with sodium hydroxide.

P9: An aqueous solution obtained by further adjusting a 5% dilute aqueous solution of Aqualic GL366 to pH 13 with sodium hydroxide.

P10: An aqueous solution obtained by further adjusting a 5% dilute aqueous solution of a commercially available aqueous polyacrylic acid solution (molecular weight 2,000, manufactured by Toagosei Co., Ltd., trade name "Aron A-210") to pH 2 with sulfuric acid.

P11: An aqueous solution obtained by further adjusting a 5% dilute aqueous solution of Aron A-210 to pH 3 with sulfuric acid.

P12: An aqueous solution obtained by further adjusting a 5% dilute aqueous solution of Aron A-210 to pH 12 with sodium hydroxide.

P13: An aqueous solution obtained by further adjusting a 5% dilute aqueous solution of Aron A-210 to pH 13 with sodium hydroxide.

P14: An aqueous solution obtained by further adjusting a 5% dilute aqueous solution of a commercially available aqueous polyacrylic acid solution (molecular weight 50,000, manufactured by NIPPON SHOKUBAI CO., LTD., trade name "Aqualic DL453") to pH 3 with sulfuric acid.

P15: An aqueous solution obtained by further adjusting a 5% dilute aqueous solution of Aqualic DL453 to pH 4 with sulfuric acid.

P16: An aqueous solution obtained by further adjusting a 5% dilute aqueous solution of Aqualic DL453 to pH 13 with sodium hydroxide.

Example 1

<Step 1>

Into a test tube equipped with a magnetic stirrer were charged 2.34 g (24.4 mmol) of a 35.5% (by weight) aqueous hydrogen peroxide solution, 123 mg (0.24 mmol) of methyltrioctyl ammonium chloride, 80 mg (0.24 mmol) of a sodium tungstate dihydrate, and 141 mg (0.6 mmol) of a 42.5% (by weight) aqueous phosphoric acid solution, and the mixture was stirred at room temperature for 30 minutes to prepare an aqueous catalyst solution. Then, 2.69 g (12.2 mmol) of a diolefin compound (*1) represented by the following structure and 2.69 g of toluene were added to the aqueous catalyst solution, and the mixture was subjected to oxidation reaction with stirring at 50° C. for 10 hours. Among two phases separated into an aqueous phase and an organic phase after the completion of the reaction, the organic phase was served as an organic solution (A). The remaining amount of the methyltrioctyl ammonium chloride in the organic solution (A) was 18053 ppm.

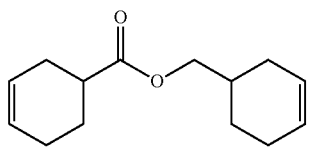

[Formula 18]

<Step 2>

To the organic solution (A) was added 4.40 g of a 2% aqueous solution of sodium hydroxide (NaOH) corresponding to 10 equivalents relative to the sodium tungstate dihydrate, and the mixture was stirred and allowed to stand to separate it into two phases of an aqueous phase and an organic phase, among which the organic phase was served as an organic solution (B).

<Step 3>

To the organic solution (B) was added 4.90 g of the aqueous polymer solution P1, and the mixture was stirred and allowed to stand to separate it into two phases of an aqueous phase and an organic phase, among which the organic phase was served as an organic solution (C) containing a diepoxy compound (**1) represented by the following structure. The purity of the diepoxy compound, and the residual amount and removal rate of the quaternary salt compound are shown in Table 1.

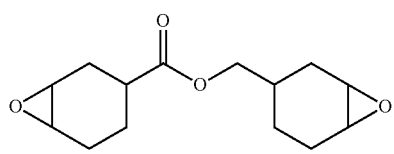

[Formula 19]

Example 2

An organic solution (C) containing the diepoxy compound (**1) was obtained in the same manner as in Example 1 except that the aqueous polymer solution P1 (4.90 g) used in the step 3 was replaced by the aqueous polymer solution P6 (4.90 g). The results are shown in Table 1.

Example 3

An organic solution (C) containing the diepoxy compound (**1) was obtained in the same manner as in Example 1 except that the aqueous polymer solution P1 (4.90 g) used in the step 3 was replaced by the aqueous polymer solution P10 (4.90 g). The results are shown in Table 1.

Example 4

An organic solution (C) containing the diepoxy compound (**1) was obtained in the same manner as in Example 1 except that the methyltrioctyl ammonium chloride (123 mg, 0.24 mmol) used in the step 1 was replaced by dialkyldimethyl ammonium chloride (a mixture of C8 to C18 alkyl chains) (146 mg, 0.24 mmol). The results are shown in Table 1.

Example 5

An organic solution (C) containing the diepoxy compound (**1) was obtained in the same manner as in Example 1 except that the methyltrioctyl ammonium chloride (123 mg, 0.24 mmol) used in the step 1 was replaced by didecyldimethyl ammonium chloride (146 mg, 0.24 mmol). The results are shown in Table 1.

Example 6

An organic solution (C) containing the diepoxy compound (**1) was obtained in the same manner as in Example 1 except that the methyltrioctyl ammonium chloride (123 mg, 0.24 mmol) used in the step 1 was replaced by didecyldimethyl ammonium chloride (110 mg, 0.24 mmol) and the aqueous polymer solution P1 (4.90 g) used in the step 3 was replaced by the aqueous polymer solution P6 (4.00 g). The results are shown in Table 1.

Comparative Example 1

An organic solution (C) containing the diepoxy compound (**1) was obtained in the same manner as in Example 1 except that the step 2 was omitted and the organic solution (A) obtained in the step 1 was regarded as the organic solution (B). The results are shown in Table 1.

Comparative Example 2

An organic solution (C) containing the diepoxy compound (**1) was obtained in the same manner as in Example 1 except that the aqueous polymer solution P1 (4.90 g) used in the step 3 was replaced by the aqueous polymer solution P4 (4.90 g). The results are shown in Table 1.

Comparative Example 3

An organic solution (C) containing the diepoxy compound (**1) was obtained in the same manner as in Example 1 except that the step 3 was omitted. In this comparative example, the organic solution (B) obtained in the step 2 was regarded as the organic solution (C). The results are shown in Table 1.

Comparative Example 4

An organic solution (C) containing the diepoxy compound (**1) was obtained in the same manner as in Example 1 except that the methyltrioctyl ammonium chloride (123 mg, 0.24 mmol) used in the step 1 was replaced by didecyldimethyl ammonium chloride (110 mg, 0.24 mmol) and the step 2 was omitted. In this comparative example, the organic solution (A) obtained in the step 1 was regarded as the organic solution (B). The results are shown in Table 1.

Example Comparative Example 5

An organic solution (C) containing the diepoxy compound (**1) was obtained in the same manner as in Example 1 except that the methyltrioctyl ammonium chloride (123 mg, 0.24 mmol) used in the step 1 was replaced by didecyldimethyl ammonium chloride (110 mg, 0.24 mmol) and the aqueous polymer solution P1 (4.90 g) used in the step 3 was replaced by the aqueous polymer solution P4 (4.00 g). The results are shown in Table 1.

TABLE 1

| | | Step 1 Organic solution (A) | | | | Step 2 In-organic alkali solution | Step 3 | | | | | Organic solution (C) Quaternary salt compound | |
|---|---|---|---|---|---|---|---|---|---|---|---|---|---|
| | | Isopoly acid | Hetero atom donor | Quaternary salt compound | | | Aqueous polymer solution | | | | Epoxy compound | | Removal rate |
| | Olefin | | | Kind | ppm | | Symbol | Kind | Mn | pH | Kind | Purity | ppm |
| Example 1 | *1 | WA-Na | PA | (Oct)$_3$MeN$^+$Cl$^-$ | 18053 | NaOH | P1 | A-10SL | 6000 | 3 | **1 | 98% | 1093 | 93.9 |
| Example 2 | *1 | WA-Na | PA | (Oct)$_3$MeN$^+$Cl$^-$ | 18053 | NaOH | P6 | GL366 | 6000 | 3 | **1 | 98% | 3366 | 81.4 |
| Example 3 | *1 | WA-Na | PA | (Oct)$_3$MeN$^+$Cl$^-$ | 18053 | NaOH | P10 | A-210 | 2000 | 2 | **1 | 98% | 4675 | 74.1 |
| Example 4 | *1 | WA-Na | PA | R$_2$(Me)$_2$N$^+$Cl$^-$(R = C8-18) | 20638 | NaOH | P1 | A-10SL | 6000 | 3 | **1 | 98% | 929 | 95.5 |
| Example 5 | *1 | WA-Na | PA | (Decyl)$_2$(Me)$_2$N$^+$Cl$^-$ | 9564 | NaOH | P1 | A-10SL | 6000 | 3 | **1 | 98% | 437 | 95.4 |
| Example 6 | *1 | WA-Na | PA | (Decyl)$_2$(Me)$_2$N$^+$Cl$^-$ | 9564 | NaOH | P6 | GL366 | 6000 | 3 | **1 | 98% | 1233 | 87.1 |
| Comparative Example 1 | *1 | WA-Na | PA | (Oct)$_3$MeN$^+$Cl$^-$ | 18053 | — | P1 | A-10SL | 6000 | 3 | **1 | 98% | 13903 | 23.0 |
| Comparative Example 2 | *1 | WA-Na | PA | (Oct)$_3$MeN$^+$Cl$^-$ | 18053 | NaOH | P4 | A-10SL | 6000 | 13 | **1 | 96% | 18002 | 0.3 |
| Comparative Example 3 | *1 | WA-Na | PA | (Oct)$_3$MeN$^+$Cl$^-$ | 18053 | NaOH | | — | | | **1 | 96% | 17995 | 0.3 |
| Comparative Example 4 | *1 | WA-Na | PA | (Decyl)$_2$(Me)$_2$N$^+$Cl$^-$ | 9564 | — | P1 | A-10SL | 6000 | 3 | **1 | 96% | 9352 | 2.2 |
| Comparative Example 5 | *1 | WA-Na | PA | (Decyl)$_2$(Me)$_2$N$^+$Cl$^-$ | 9564 | NaOH | P4 | A-10SL | 6000 | 13 | **1 | 96% | 9411 | 1.6 |

In Table 1, WA-Na represents sodium tungstate dihydrate and PA represents phosphoric acid, respectively (the same shall apply to Tables 2 to 7).

Example 7

<Step 1>

Into a test tube equipped with a magnetic stirrer were charged 3.86 g (40.3 mmol) of a 35.5% (by weight) aqueous hydrogen peroxide solution, 0.48 g (0.81 mmol) of dialkyldimethyl ammonium chloride (a mixture of C8 to C18 alkyl chains), 0.27 g (0.81 mmol) of a sodium tungstate dihydrate, and 0.46 g (2.01 mmol) of a 42.5% (by weight) aqueous phosphoric acid solution, and the mixture was stirred at room temperature for 30 minutes to prepare an aqueous catalyst solution. Then, 5.00 g (40.3 mmol) of a monoolefin compound (*2) represented by the following structure and 5.00 g of toluene were added to the aqueous catalyst solution, and the mixture was subjected to oxidation reaction with stirring at 50° C. for 10 hours. Among two phases separated into an aqueous phase and an organic phase after the completion of the reaction, the organic phase was served as an organic solution (A). The remaining amount of the dialkyldimethyl ammonium chloride in the organic solution (A) was 18721 ppm.

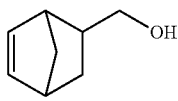

[Formula 20]

<Step 2>

To the organic solution (A) was added 16.1 g of a 2% aqueous solution of sodium hydroxide (NaOH) corresponding to 10 equivalents relative to the sodium tungstate dihydrate, and the mixture was stirred and allowed to stand to separate it into two phases of an aqueous phase and an organic phase, among which the organic phase was served as an organic solution (B).

<Step 3>

To the organic solution (B) was added 19.2 g of the aqueous polymer solution P1, and the mixture was stirred and allowed to stand to separate it into two phases of an aqueous phase and an organic phase, among which the organic phase was served as an organic solution (C) containing a monoepoxy compound (**2) represented by the following structure. The purity of the monoepoxy compound, and the residual amount and removal rate of the quaternary salt compound are shown in Table 2.

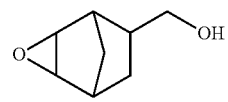

[Formula 21]

Example 8

An organic solution (C) containing the monoepoxy compound (**2) was obtained in the same manner as in Example 7 except that the aqueous polymer solution P1 (19.2 g) used in the step 3 was replaced by the aqueous polymer solution P6 (19.2 g). The results are shown in Table 2.

Comparative Example 6

An organic solution (C) containing the monoepoxy compound (**2) was obtained in the same manner as in Example 7 except that the step 3 was omitted. In this comparative example, the organic solution (B) obtained in the step 2 was regarded as the organic solution (C). The results are shown in Table 2.

Comparative Example 7

An organic solution (C) containing the monoepoxy compound (**2) was obtained in the same manner as in Example 1 except that the aqueous polymer solution P1 (4.90 g) was replaced by the aqueous polymer solution P4 (19.2 g). The results are shown in Table 2.

(**3) represented by the following structure. The purity of the diepoxy compound, and the residual amount and removal rate of the quaternary salt compound are shown in Table 3.

TABLE 2

| | Step 1 | | | | | Step 2 | Step 3 | | | | | | |
|---|---|---|---|---|---|---|---|---|---|---|---|---|---|
| | Organic solution (A) | | | | | In-organic alkali solution | Organic solution (C) | | | | | | |
| | | | | Quaternary salt compound | | | Aqueous polymer solution | | | | Epoxy compound | | Quaternary salt compound |
| | | Hetero | | | | | | | | | | | Removal |
| | Isopoly | atom | | | | | | | | | | | |
| | Olefin | acid | donor | Kind | ppm | solution | Symbol | Kind | Mn | pH | Kind | Purity | ppm | rate |
| Example 7 | *2 | WA-Na | PA | R₂(Me)₂N⁺Cl⁻(R = C8-18) | 18721 | NaOH | P1 | A-10SL | 6000 | 3 | **2 | 99% | 4819 | 74.3 |
| Example 8 | *2 | WA-Na | PA | R₂(Me)₂N⁺Cl⁻(R = C8-18) | 18721 | NaOH | P6 | GL366 | 6000 | 3 | **2 | 99% | 5178 | 72.3 |
| Comparative Example 6 | *2 | WA-Na | PA | R₂(Me)₂N⁺Cl⁻(R = C8-18) | 18721 | NaOH | | — | | | **2 | 95% | 18032 | 3.7 |
| Comparative Example 7 | *2 | WA-Na | PA | R₂(Me)₂N⁺Cl⁻(R = C8-18) | 18721 | NaOH | P4 | A-10SL | 6000 | 13 | **2 | 95% | 16598 | 11.3 |

Example 9

<Step 1>

Into a test tube equipped with a magnetic stirrer were charged 9.06 g (94.5 mmol) of a 35.5% (by weight) aqueous hydrogen peroxide solution, 0.19 g (0.38 mmol) of methyltrioctyl ammonium chloride, 0.12 g (0.38 mmol) of a sodium tungstate dihydrate, and 0.22 g (0.95 mmol) of a 42.5% (by weight) aqueous phosphoric acid solution, and the mixture was stirred at room temperature for 30 minutes to prepare an aqueous catalyst solution. Then, 5.00 g (37.8 mmol) of a diolefin compound (*3) represented by the following structure and 5.00 g of toluene were added to the aqueous catalyst solution, and the mixture was subjected to oxidation reaction with stirring at 50° C. for 10 hours. Among two phases separated into an aqueous phase and an organic phase after the completion of the reaction, the organic phase was served as an organic solution (A). The remaining amount of the methyltrioctyl ammonium chloride in the organic solution (A) was 20272 ppm.

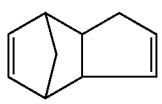

[Formula 22]

<Step 2>

To the organic solution (A) was added 7.70 g of a 2% aqueous solution of sodium hydroxide (NaOH) corresponding to 10 equivalents relative to the sodium tungstate dihydrate, and the mixture was stirred and allowed to stand to separate it into two phases of an aqueous phase and an organic phase, among which the organic phase was served as an organic solution (B).

<Step 3>

To the organic solution (B) was added 7.70 g of the aqueous polymer solution P1, and the mixture was stirred and allowed to stand to separate it into two phases of an aqueous phase and an organic phase, among which the organic phase was served as an organic solution (C) containing a diepoxy compound

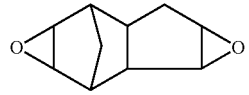

[Formula 23]

Example 10

An organic solution (C) containing the diepoxy compound (**3) was obtained in the same manner as in Example 9 except that the aqueous polymer solution P1 (7.70 g) used in the step 3 was replaced by the aqueous polymer solution P6 (7.70 g). The results are shown in Table 3.

Example 11

An organic solution (C) containing the diepoxy compound (**3) was obtained in the same manner as in Example 9 except that the methyltrioctyl ammonium chloride (0.19 g, 0.38 mmol) used in the step 1 was replaced by didecyldimethyl ammonium chloride (0.17 g, 0.38 mmol) and the aqueous polymer solution P1 (7.70 g) used in the step 3 was replaced by the aqueous polymer solution P10 (6.90 g). The results are shown in Table 3.

Example 12

An organic solution (C) containing the diepoxy compound (**3) was obtained in the same manner as in Example 9 except that the methyltrioctyl ammonium chloride (0.19 g, 0.38 mmol) used in the step 1 was replaced by didecyldimethyl ammonium chloride (0.17 g, 0.38 mmol) and the aqueous polymer solution P1 (7.70 g) used in the step 3 was replaced by the aqueous polymer solution P5 (6.90 g). The results are shown in Table 3.

Comparative Example 8

An organic solution (C) containing the diepoxy compound (**3) was obtained in the same manner as in Example 9 except that the step 3 was omitted. In this comparative example, the organic solution (B) obtained in the step 2 was regarded as the organic solution (C). The results are shown in Table 3.

Comparative Example 9

An organic solution (C) containing the diepoxy compound (**3) was obtained in the same manner as in Example 9 except that the aqueous polymer solution P1 (7.70 g) used in the step 3 was replaced by the aqueous polymer solution P4 (7.70 g). The results are shown in Table 3.

Comparative Example 10

An organic solution (C) containing the diepoxy compound (**3) was obtained in the same manner as in Example 9 except that the methyltrioctyl ammonium chloride (0.19 g, 0.38 mmol) used in the step 1 was replaced by didecyldimethyl ammonium chloride (0.17 g, 0.38 mmol) and the aqueous polymer solution P1 (7.70 g) used in the step 3 was replaced by the aqueous polymer solution P12 (6.90 g). The results are shown in Table 3.

Comparative Example 11

An organic solution (C) containing the diepoxy compound (**3) was obtained in the same manner as in Example 9 except that the methyltrioctyl ammonium chloride (0.19 g, 0.38 mmol) used in the step 1 was replaced by didecyldimethyl ammonium chloride (0.17 g, 0.38 mmol) and the aqueous polymer solution P1 (7.70 g) used in the step 3 was replaced by the aqueous polymer solution P8 (6.90 g). The results are shown in Table 3.

Comparative Example 12

An organic solution (C) containing the diepoxy compound (**3) was obtained in the same manner as in Example 9 except that the methyltrioctyl ammonium chloride (0.19 g, 0.38 mmol) used in the step 1 was replaced by didecyldimethyl ammonium chloride (0.17 g, 0.38 mmol) and the aqueous polymer solution P1 (7.70 g) used in the step 3 was replaced by the aqueous polymer solution P4 (6.90 g). The results are shown in Table 3.

Comparative Example 13

An organic solution (C) containing the diepoxy compound (**3) was obtained in the same manner as in Example 9 except that the methyltrioctyl ammonium chloride (0.19 g, 0.38 mmol) used in the step 1 was replaced by didecyldimethyl ammonium chloride (0.17 g, 0.38 mmol) and the step 2 was omitted. In this comparative example, the organic solution (A) obtained in the step 1 was regarded as the organic solution (B). The results are shown in Table 3.

Example 13

<Step 1>
Into a test tube equipped with a magnetic stirrer were charged 7.97 g (83.2 mmol) of a 35.5% (by weight) aqueous hydrogen peroxide solution, 0.17 g (0.33 mmol) of methyltrioctyl ammonium chloride, 0.11 g (0.33 mmol) of a sodium tungstate dihydrate, and 0.19 g (0.83 mmol) of a 42.5% (by weight) aqueous phosphoric acid solution, and the mixture was stirred at room temperature for 30 minutes to prepare an aqueous catalyst solution. Then, 5.00 g (33.3 mmol) of a monoolefin compound (*4) represented by the following structure and 2.34 g of toluene were added to the aqueous catalyst solution, and the mixture was subjected to oxidation reaction with stirring at 50° C. for 10 hours. The monoolefin compound is a mixture of a compound wherein a hydroxyl group is bonded to the 5-position of the norbornane ring and a compound wherein a hydroxy group is bonded to the 6-position of the norbornane ring. Among two phases separated into an aqueous phase and an organic phase after the completion of the reaction, the organic phase was served as an organic solution (A). The remaining amount of the methyltrioctyl ammonium chloride in the organic solution (A) was 23083 ppm.

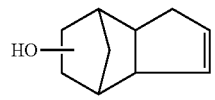

[Formula 24]

<Step 2>
To the organic solution (A) was added 6.70 g of a 2% aqueous solution of sodium hydroxide (NaOH) corresponding to 10 equivalents relative to the sodium tungstate dihydrate, and the mixture was stirred and allowed to stand to separate it into two phases of an aqueous phase and an organic phase, among which the organic phase was served as an organic solution (B).

<Step 3>
To the organic solution (B) was added 6.70 g of the aqueous polymer solution P1, and the mixture was stirred and allowed to stand to separate it into two phases of an aqueous phase and an organic phase, among which the organic phase was served as an organic solution (C) containing a monoepoxy compound (**4) represented by the following structure. The monoepoxy compound is a mixture of a compound wherein a hydroxyl group is bonded to the 5-position of the norbornane ring and a compound wherein a hydroxy group is bonded to the 6-position of the norbornane ring. The purity of the monoepoxy compound, and the residual amount and removal rate of the quaternary salt compound are shown in Table 3.

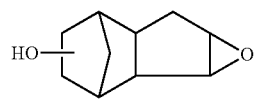

[Formula 25]

Example 14

An organic solution (C) containing the monoepoxy compound (**4) was obtained in the same manner as in Example 13 except that the aqueous polymer solution P1 (6.70 g) used in the step 3 was replaced by the aqueous polymer solution P6 (6.70 g). The results are shown in Table 3.

Comparative Example 14

An organic solution (C) containing the monoepoxy compound (**4) was obtained in the same manner as in Example 13 except that the step 3 was omitted. In this comparative example, the organic solution (B) obtained in the step 2 was regarded as the organic solution (C). The results are shown in Table 3.

Comparative Example 15

An organic solution (C) containing the monoepoxy compound (**4) was obtained in the same manner as in Example 13 except that the aqueous polymer solution P1 (6.70 g) used in the step 3 was replaced by the aqueous polymer solution P4 (6.70 g). The results are shown in Table 3.

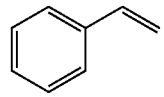

[Formula 26]

<Step 2>

To the organic solution (A) was added 19.2 g of a 2% aqueous solution of sodium hydroxide (NaOH) corresponding to 10 equivalents relative to the sodium tungstate dihy-

TABLE 3

| | | Step 1 | | | | Step 2 | | Step 3 | | | | | |
|---|---|---|---|---|---|---|---|---|---|---|---|---|---|
| | | Organic solution (A) | | | | In- | | | | Organic solution (C) | | | |
| | | | | | | organic | | | | Epoxy compound | | Quaternary salt compound | |
| | | | Hetero atom donor | Quaternary salt compound | | alkali | Aqueous polymer solution | | | | Pu- | | Removal |
| | Olefin | Isopoly acid | | Kind | ppm | solution | Symbol | Kind | Mn | pH | Kind | rity | ppm | rate |
| Example 9 | *3 | WA-Na | PA | (Oct)₃MeN⁺Cl⁻ | 20272 | NaOH | P1 | A-10SL | 6000 | 3 | **3 | 99% | 6619 | 67.3 |
| Example 10 | *3 | WA-Na | PA | (Oct)₃MeN⁺Cl⁻ | 20272 | NaOH | P6 | GL366 | 6000 | 3 | **3 | 99% | 6619 | 67.3 |
| Example 11 | *3 | WA-Na | PA | (Decyl)₂(Me)₂N⁺Cl⁻ | 12806 | NaOH | P10 | A-210 | 2000 | 2 | **3 | 99% | 543 | 95.8 |
| Example 12 | *3 | WA-Na | PA | (Decyl)₂(Me)₂N⁺Cl⁻ | 12806 | NaOH | P5 | GL366 | 6000 | 2 | **3 | 99% | 875 | 93.2 |
| Comparative Example 8 | *3 | WA-Na | PA | (Oct)₃MeN⁺Cl⁻ | 20272 | NaOH | | — | | | **3 | 97% | 20191 | 0.4 |
| Comparative Example 9 | *3 | WA-Na | PA | (Oct)₃MeN⁺Cl⁻ | 20272 | NaOH | P4 | A-10SL | 6000 | 13 | **3 | 97% | 20002 | 1.3 |
| Comparative Example 10 | *3 | WA-Na | PA | (Decyl)₂(Me)₂N⁺Cl⁻ | 12806 | NaOH | P12 | A-210 | 2000 | 12 | **3 | 97% | 11917 | 6.9 |
| Comparative Example 11 | *3 | WA-Na | PA | (Decyl)₂(Me)₂N⁺Cl⁻ | 12806 | NaOH | P8 | GL366 | 6000 | 12 | **3 | 97% | 12099 | 5.5 |
| Comparative Example 12 | *3 | WA-Na | PA | (Decyl)₂(Me)₂N⁺Cl⁻ | 12806 | NaOH | P4 | A-10SL | 6000 | 13 | **3 | 97% | 12748 | 0.5 |
| Comparative Example 13 | *3 | WA-Na | PA | (Decyl)₂(Me)₂N⁺Cl⁻ | 12806 | — | P1 | A-10SL | 6000 | 3 | **3 | 97% | 12477 | 2.6 |
| Example 13 | *4 | WA-Na | PA | (Oct)₃MeN⁺Cl⁻ | 23083 | NaOH | P1 | A-10SL | 6000 | 3 | **4 | 99% | 4530 | 80.4 |
| Example 14 | *4 | WA-Na | PA | (Oct)₃MeN⁺Cl⁻ | 23083 | NaOH | P6 | GL366 | 6000 | 3 | **4 | 99% | 4530 | 80.4 |
| Comparative Example 14 | *4 | WA-Na | PA | (Oct)₃MeN⁺Cl⁻ | 23083 | NaOH | | — | | | **4 | 96% | 23083 | 0 |
| Comparative Example 15 | *4 | WA-Na | PA | (Oct)₃MeN⁺Cl⁻ | 23083 | NaOH | P4 | A-10SL | 6000 | 13 | **4 | 96% | 20837 | 9.7 |

Example 15

<Step 1>

Into a test tube equipped with a magnetic stirrer were charged 4.60 g (48.0 mmol) of a 35.5% (by weight) aqueous hydrogen peroxide solution, 0.49 g (0.96 mmol) of methyltrioctyl ammonium chloride, 0.32 g (0.96 mmol) of a sodium tungstate dihydrate, 0.55 g (2.40 mmol) of a 42.5% (by weight) aqueous phosphoric acid solution, and 2.04 g (14.4 mmol) of sodium sulfate, and the mixture was stirred at room temperature for 30 minutes to prepare an aqueous catalyst solution. Then, 5.00 g (48.0 mmol) of a monoolefin compound (*5) represented by the following structure and 5.00 g of toluene were added to the aqueous catalyst solution, and the mixture was subjected to oxidation reaction with stirring at 50° C. for 10 hours. Among two phases separated into an aqueous phase and an organic phase after the completion of the reaction, the organic phase was served as an organic solution (A). The remaining amount of the methyltrioctyl ammonium chloride in the organic solution (A) was 35421 ppm.

drate, and the mixture was stirred and allowed to stand to separate it into two phases of an aqueous phase and an organic phase, among which the organic phase was served as an organic solution (B).

<Step 3>

To the organic solution (B) was added 19.4 g of the aqueous polymer solution P2, and the mixture was stirred and allowed to stand to separate it into two phases of an aqueous phase and an organic phase, among which the organic phase was served as an organic solution (C) containing a monoepoxy compound (**5) represented by the following structure. The purity of the monoepoxy compound, and the residual amount and removal rate of the quaternary salt compound are shown in Table 4.

[Formula 27]

Example 16

An organic solution (C) containing the monoepoxy compound (**5) was obtained in the same manner as in Example 15 except that the aqueous polymer solution P2 (19.4 g) used in the step 3 was replaced by the aqueous polymer solution P7 (19.4 g). The results are shown in Table 4.

Comparative Example 16

An organic solution (C) containing the monoepoxy compound (**5) was obtained in the same manner as in Example 15 except that the step 3 was omitted. In this comparative example, the organic solution (B) obtained in the step 2 was regarded as the organic solution (C). The results are shown in Table 4.

Comparative Example 17

An organic solution (C) containing the monoepoxy compound (**5) was obtained in the same manner as in Example 15 except that the aqueous polymer solution P2 (19.4 g) used in the step 3 was replaced by the aqueous polymer solution P4 (19.4 g). The results are shown in Table 4.

Example 17

<Step 1>
Into a test tube equipped with a magnetic stirrer were charged 3.92 g (40.9 mmol) of a 35.5% (by weight) aqueous hydrogen peroxide solution, 0.41 g (0.82 mmol) of methyltrioctyl ammonium chloride, 0.27 g (0.82 mmol) of a sodium tungstate dihydrate, 0.47 g (2.05 mmol) of a 42.5% (by weight) aqueous phosphoric acid solution, and 1.74 g (12.3 mmol) of a sodium sulfate, and the mixture was stirred at room temperature for 30 minutes to prepare an aqueous catalyst solution. Then, 5.00 g (40.9 mmol) of a monoolefin compound (*6) represented by the following structure and 5.00 g of toluene were added to the aqueous catalyst solution, and the mixture was subjected to oxidation reaction with stirring at 50° C. for 10 hours. Among two phases separated into an aqueous phase and an organic phase after the completion of the reaction, the organic phase was served as an organic solution (A). The remaining amount of the methyltrioctyl ammonium chloride in the organic solution (A) was 31684 ppm.

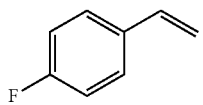

[Formula 28]

<Step 2>
To the organic solution (A) was added 16.4 g of a 2% aqueous solution of sodium hydroxide (NaOH) corresponding to 10 equivalents relative to the sodium tungstate dihydrate, and the mixture was stirred and allowed to stand to separate it into two phases of an aqueous phase and an organic phase, among which the organic phase was served as an organic solution (B).

<Step 3>
To the organic solution (B) was added 16.5 g of the aqueous polymer solution P11, and the mixture was stirred and allowed to stand to separate it into two phases of an aqueous phase and an organic phase, among which the organic phase was served as an organic solution (C) containing a monoepoxy compound (**6) represented by the following structure. The purity of the monoepoxy compound, and the residual amount and removal rate of the quaternary salt compound are shown in Table 4.

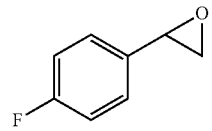

[Formula 29]

Example 18

An organic solution (C) containing the monoepoxy compound (**6) was obtained in the same manner as in Example 17 except that the aqueous polymer solution P11 (16.5 g) used in the step 3 was replaced by the aqueous polymer solution P6 (16.5 g). The results are shown in Table 4.

Comparative Example 18

An organic solution (C) containing the monoepoxy compound (**6) was obtained in the same manner as in Example 17 except that the step 3 was omitted. In this comparative example, the organic solution (B) obtained in the step 2 was regarded as the organic solution (C). The results are shown in Table 4.

Example 19

An organic solution (C) containing the monoepoxy compound (**6) was obtained in the same manner as in Example 17 except that the aqueous polymer solution P11 (16.5 g) used in the step 3 was replaced by the aqueous polymer solution P13 (16.5 g). The results are shown in Table 4.

Example 19

<Step 1>
Into a test tube equipped with a magnetic stirrer were charged 3.46 g (36.1 mmol) of a 35.5% (by weight) aqueous hydrogen peroxide solution, 0.40 g (0.72 mmol) of dialkyldimethylammonium chloride (a mixture of C8 to C18 alkyl chains), 0.23 g (0.72 mmol) of a sodium tungstate dihydrate, 0.41 g (1.80 mmol) of a 42.5% (by weight) aqueous phosphoric acid solution, and 1.53 g (10.8 mmol) of a sodium sulfate, and the mixture was stirred at room temperature for 30 minutes to prepare an aqueous catalyst solution. Then, 5.00 g (36.1 mmol) of a monoolefin compound (*7) represented by the following structure and 5.00 g of toluene were added to the aqueous catalyst solution, and the mixture was subjected to oxidation reaction with stirring at 50° C. for 10 hours. Among two phases separated into an aqueous phase and an organic phase after the completion of the reaction, the organic phase was served as an organic solution (A). The remaining amount of the dialkyldimethyl ammonium chloride in the organic solution

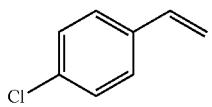

[Formula 30]

<Step 2>
To the organic solution (A) was added 14.4 g of a 2% aqueous solution of sodium hydroxide (NaOH) corresponding to 10 equivalents relative to the sodium tungstate dihydrate, and the mixture was stirred and allowed to stand to separate it into two phases of an aqueous phase and an organic phase, among which the organic phase was served as an organic solution (B).

<Step 3>
To the organic solution (B) was added 16.1 g of the aqueous polymer solution P1, and the mixture was stirred and allowed to stand to separate it into two phases of an aqueous phase and an organic phase, among which the organic phase was served as an organic solution (C) containing a monoepoxy compound (**7) represented by the following structure. The purity of the monoepoxy compound, and the residual amount and removal rate of the quaternary salt compound are shown in Table 4.

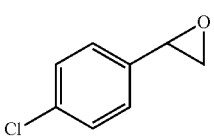

[Formula 31]

Example 20

An organic solution (C) containing the monoepoxy compound (**7) was obtained in the same manner as in Example 19 except that the aqueous polymer solution P1 (16.1 g) used in the step 3 was replaced by the aqueous polymer solution P6 (16.1 g). The results are shown in Table 4.

Comparative Example 20

An organic solution (C) containing the monoepoxy compound (**7) was obtained in the same manner as in Example 19 except that the step 3 was omitted. In this comparative example, the organic solution (B) obtained in the step 2 was regarded as the organic solution (C). The results are shown in Table 4.

Comparative Example 21

An organic solution (C) containing the monoepoxy compound (**7) was obtained in the same manner as in Example 19 except that the aqueous polymer solution P1 (16.1 g) used in the step 3 was replaced by the aqueous polymer solution P4 (16.1 g). The results are shown in Table 4.

Comparative Example 22

An organic solution (C) containing the monoepoxy compound (**7) was obtained in the same manner as in Example 19 except that the step 2 was omitted and the aqueous polymer solution P1 (16.1 g) used in the step 3 was replaced by the aqueous polymer solution P6 (16.1 g). In this comparative example, the organic solution (A) obtained in the step 2 was regarded as the organic solution (B). The results are shown in Table 4.

Example 21

<Step 1>
Into a test tube equipped with a magnetic stirrer were charged 2.61 g (27.3 mmol) of a 35.5% (by weight) aqueous hydrogen peroxide solution, 0.25 mg (0.55 mmol) of didecyldimethyl ammonium chloride, 0.18 g (0.55 mmol) of a sodium tungstate dihydrate, 0.31 g (1.37 mmol) of a 42.5% (by weight) aqueous phosphoric acid solution, and 1.16 g (8.19 mmol) of sodium sulfate, and the mixture was stirred at room temperature for 30 minutes to prepare an aqueous catalyst solution. Then, 5.00 g (27.3 mmol) of a monoolefin compound (*8) represented by the following structure and 5.00 g of toluene were added to the aqueous catalyst solution, and the mixture was subjected to oxidation reaction with stirring at 50° C. for 10 hours. Among two phases separated into an aqueous phase and an organic phase after the completion of the reaction, the organic phase was served as an organic solution (A). The remaining amount of the didecyl dimethylammonium chloride in the organic solution (A) was 22489 ppm.

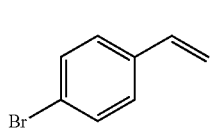

[Formula 32]

<Step 2>
To the organic solution (A) was added 10.9 g of a 2% aqueous solution of sodium hydroxide (NaOH) corresponding to 10 equivalents relative to the sodium tungstate dihydrate, and the mixture was stirred and allowed to stand to separate it into two phases of an aqueous phase and an organic phase, among which the organic phase was served as an organic solution (B).

<Step 3>
To the organic solution (B) was added 9.9 g of the aqueous polymer solution P1, and the mixture was stirred and allowed to stand to separate it into two phases of an aqueous phase and an organic phase, among which the organic phase was served as an organic solution (C) containing a monoepoxy compound (**8) represented by the following structure. The purity of the monoepoxy compound, and the residual amount and removal rate of the quaternary salt compound are shown in Table 4.

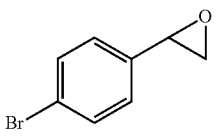

[Formula 33]

Example 22

An organic solution (C) containing the monoepoxy compound (**8) was obtained in the same manner as in Example 21 except that the aqueous polymer solution P1 (9.9 g) used in the step 3 was replaced by the aqueous polymer solution P6 (9.9 g). The results are shown in Table 4.

Comparative Example 23

An organic solution (C) containing the monoepoxy compound (**8) was obtained in the same manner as in Example 21 except that the step 3 was omitted. In this comparative example, the organic solution (B) obtained in the step 2 was regarded as the organic solution (C). The results are shown in Table 4.

Comparative Example 24

An organic solution (C) containing the monoepoxy compound (**8) was obtained in the same manner as in Example 21 except that the aqueous polymer solution P1 (9.9 g) used in the step 3 was replaced by the aqueous polymer solution P4 (9.9 g). The results are shown in Table 4.

Example 23

<Step 1>
Into a test tube equipped with a magnetic stirrer were charged 4.05 g (42.3 mmol) of a 35.5% (by weight) aqueous hydrogen peroxide solution, 0.43 g (0.85 mmol) of methyltrioctyl ammonium chloride, 0.28 g (0.85 mmol) of a sodium tungstate dihydrate, 0.49 g (2.12 mmol) of a 42.5% (by weight) aqueous phosphoric acid solution, and 1.80 g (12.7 mmol) of sodium sulfate, and the mixture was stirred at room temperature for 30 minutes to prepare an aqueous catalyst solution. Then, 5.00 g (42.3 mmol) of a olefin compound (*9) represented by the following structure and 2.69 g of toluene were added to the aqueous catalyst solution, and the mixture was subjected to oxidation reaction with stirring at 50° C. for 10 hours. Among two phases separated into an aqueous phase and an organic phase after the completion of the reaction, the organic phase was served as an organic solution (A). The remaining amount of the methyltrioctyl ammonium chloride in the organic solution (A) was 30984 ppm.

[Formula 34]

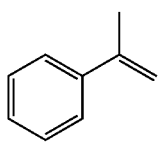

<Step 2>
To the organic solution (A) was added 16.9 g of a 2% aqueous solution of sodium hydroxide (NaOH) corresponding to 10 equivalents relative to the sodium tungstate dihydrate, and the mixture was stirred and allowed to stand to separate it into two phases of an aqueous phase and an organic phase, among which the organic phase was served as an organic solution (B).

<Step 3>
To the organic solution (B) was added 17.1 g of the aqueous polymer solution P1, and the mixture was stirred and allowed to stand to separate it into two phases of an aqueous phase and an organic phase, among which the organic phase was served as an organic solution (C) containing a monoepoxy compound (**9) represented by the following structure. The purity of the monoepoxy compound, and the residual amount and removal rate of the quaternary salt compound are shown in Table 4.

[Formula 35]

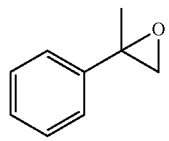

Example 24

An organic solution (C) containing the monoepoxy compound (**9) was obtained in the same manner as in Example 23 except that the aqueous polymer solution P1 (17.1 g) used in the step 3 was replaced by the aqueous polymer solution P6 (17.1 g). The results are shown in Table 4.

Comparative Example 25

An organic solution (C) containing the monoepoxy compound (**9) was obtained in the same manner as in Example 23 except that the step 3 was omitted. In this comparative example, the organic solution (B) obtained in the step 2 was regarded as the organic solution (C). The results are shown in Table 4.

Comparative Example 26

An organic solution (C) containing the monoepoxy compound (**9) was obtained in the same manner as in Example 23 except that the aqueous polymer solution P1 (17.1 g) used in the step 3 was replaced by the aqueous polymer solution P4 (17.1 g). The results are shown in Table 4.

Example 25

<Step 1>
Into a test tube equipped with a magnetic stirrer were charged 4.05 g (42.3 mmol) of a 35.5% (by weight) aqueous hydrogen peroxide solution, 0.43 g (0.85 mmol) of methyltrioctyl ammonium chloride, 0.28 g (0.85 mmol) of a sodium tungstate dihydrate, 0.49 g (2.12 mmol) of a 42.5% (by weight) aqueous phosphoric acid solution, and 1.80 g (12.7 mmol) of sodium sulfate, and the mixture was stirred at room temperature for 30 minutes to prepare an aqueous catalyst solution. Then, 5.00 g (42.3 mmol) of a diolefin compound (*10) represented by the following structure and 5.00 g of toluene were added to the aqueous catalyst solution, and the mixture was subjected to oxidation reaction with stirring at 50° C. for 10 hours. Among two phases separated into an aqueous phase and an organic phase after the completion of the reaction, the organic phase was served as an organic solution (A). The remaining amount of the methyltrioctyl ammonium chloride in the organic solution (A) was 30475 ppm.

[Formula 36]

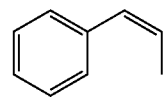

<Step 2>
To the organic solution (A) was added 16.9 g of a 2% aqueous solution of sodium hydroxide (NaOH) corresponding to 10 equivalents relative to the sodium tungstate dihydrate, and the mixture was stirred and allowed to stand to separate it into two phases of an aqueous phase and an organic phase, among which the organic phase was served as an organic solution (B).

<Step 3>

To the organic solution (B) was added 17.1 g of the aqueous polymer solution P10, and the mixture was stirred and allowed to stand to separate it into two phases of an aqueous phase and an organic phase, among which the organic phase was served as an organic solution (C) containing a monoepoxy compound (**10) represented by the following structure. The purity of the monoepoxy compound, and the residual amount and removal rate of the quaternary salt compound are shown in Table 4.

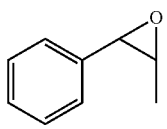

[Formula 37]

Example 26

An organic solution (C) containing the monoepoxy compound (**10) was obtained in the same manner as in Example 25 except that the aqueous polymer solution P10 (17.1 g) used in the step 3 was replaced by the aqueous polymer solution P5 (17.1 g). The results are shown in Table 4.

Comparative Example 27

An organic solution (C) containing the monoepoxy compound (**10) was obtained in the same manner as in Example 25 except that the step 3 was omitted. In this comparative example, the organic solution (B) obtained in the step 2 was regarded as the organic solution (C). The results are shown in Table 4.

Comparative Example 28

An organic solution (C) containing the monoepoxy compound (**10) was obtained in the same manner as in Example 25 except that the aqueous polymer solution P10 (17.1 g) used in the step 3 was replaced by the aqueous polymer solution P9 (17.1 g). The results are shown in Table 4.

TABLE 4

| | Step 1 | | | | | Step 2 | Step 3 | | | | | | |
|---|---|---|---|---|---|---|---|---|---|---|---|---|---|
| | Organic solution (A) | | | | | In- | Organic solution (C) | | | | | | |
| | | Hetero | | | | organic | Aqueous polymer solution | | | | Epoxy compound | Quaternary salt compound | |
| | | Isopoly | atom | Quaternary salt compound | | alkali | | | | | Pu- | | Removal |
| | Olefin | acid | donor | Kind | ppm | solution | Symbol | Kind | Mn | pH | Kind | rity | ppm | rate |
| Example 15 | *5 | WA-Na | PA | (Oct)$_3$MeN$^+$Cl$^-$ | 35421 | NaOH | P2 | A-10SL | 6000 | 4 | **5 | 85% | 5348 | 84.9 |
| Example 16 | *5 | WA-Na | PA | (Oct)$_3$MeN$^+$Cl$^-$ | 35421 | NaOH | P7 | GL366 | 6000 | 4 | **5 | 85% | 7558 | 78.7 |
| Comparative Example 16 | *5 | WA-Na | PA | (Oct)$_3$MeN$^+$Cl$^-$ | 35421 | NaOH | — | | | | **5 | 83% | 34785 | 1.8 |
| Comparative Example 17 | *5 | WA-Na | PA | (Oct)$_3$MeN$^+$Cl$^-$ | 35421 | NaOH | P4 | A-10SL | 6000 | 13 | **5 | 83% | 33471 | 5.5 |
| Example 17 | *6 | WA-Na | PA | (Oct)$_3$MeN$^+$Cl$^-$ | 31684 | NaOH | P11 | A-210 | 2000 | 3 | **6 | 74% | 2419 | 92.4 |
| Example 18 | *6 | WA-Na | PA | (Oct)$_3$MeN$^+$Cl$^-$ | 31684 | NaOH | P6 | GL366 | 6000 | 3 | **6 | 74% | 4711 | 85.1 |
| Comparative Example 18 | *6 | WA-Na | PA | (Oct)$_3$MeN$^+$Cl$^-$ | 31684 | NaOH | — | | | | **6 | 70% | 30994 | 2.2 |
| Comparative Example 19 | *6 | WA-Na | PA | (Oct)$_3$MeN$^+$Cl$^-$ | 31684 | NaOH | P13 | A-210 | 2000 | 13 | **6 | 70% | 31574 | 0.3 |
| Example 19 | *7 | WA-Na | PA | R$_2$(Me)$_2$N$^+$Cl$^-$(R = C8-18) | 27441 | NaOH | P1 | A-10SL | 6000 | 3 | **7 | 88% | 2116 | 92.3 |
| Example 20 | *7 | WA-Na | PA | R$_2$(Me)$_2$N$^+$Cl$^-$(R = C8-18) | 27441 | NaOH | P6 | GL366 | 6000 | 3 | **7 | 88% | 2954 | 89.2 |
| Comparative Example 20 | *7 | WA-Na | PA | R$_2$(Me)$_2$N$^+$Cl$^-$(R = C8-18) | 27441 | NaOH | — | | | | **7 | 86% | 26157 | 4.7 |
| Comparative Example 21 | *7 | WA-Na | PA | R$_2$(Me)$_2$N$^+$Cl$^-$(R = C8-18) | 27441 | NaOH | P4 | A-10SL | 6000 | 13 | **7 | 86% | 25179 | 8.2 |
| Comparative Example 22 | *7 | WA-Na | PA | R$_2$(Me)$_2$N$^+$Cl$^-$(R = C8-18) | 27441 | — | P6 | GL366 | 6000 | 3 | **7 | 86% | 27358 | 0.3 |
| Example 21 | *8 | WA-Na | PA | (Decyl)$_2$(Me)$_2$N$^+$Cl$^-$ | 22489 | NaOH | P1 | A-10SL | 6000 | 3 | **8 | 81% | 4513 | 79.9 |
| Example 22 | *8 | WA-Na | PA | (Decyl)$_2$(Me)$_2$N$^+$Cl$^-$ | 22489 | NaOH | P6 | GL366 | 6000 | 3 | **8 | 81% | 5946 | 73.6 |
| Comparative Example 23 | *8 | WA-Na | PA | (Decyl)$_2$(Me)$_2$N$^+$Cl$^-$ | 22489 | NaOH | — | | | | **8 | 78% | 21598 | 4.0 |
| Comparative Example 24 | *8 | WA-Na | PA | (Decyl)$_2$(Me)$_2$N$^+$Cl$^-$ | 22489 | NaOH | P4 | A-10SL | 6000 | 13 | **8 | 78% | 20147 | 10.4 |
| Example 23 | *9 | WA-Na | PA | (Oct)$_3$MeN$^+$Cl$^-$ | 30984 | NaOH | P1 | A-10SL | 6000 | 3 | **9 | 96% | 1549 | 95.0 |
| Example 24 | *9 | WA-Na | PA | (Oct)$_3$MeN$^+$Cl$^-$ | 30984 | NaOH | P6 | GL366 | 6000 | 3 | **9 | 96% | 3498 | 88.7 |
| Comparative Example 25 | *9 | WA-Na | PA | (Oct)$_3$MeN$^+$Cl$^-$ | 30984 | NaOH | — | | | | **9 | 92% | 28934 | 6.6 |
| Comparative Example 26 | *9 | WA-Na | PA | (Oct)$_3$MeN$^+$Cl$^-$ | 30984 | NaOH | P4 | A-10SL | 6000 | 13 | **9 | 92% | 29478 | 4.9 |
| Example 25 | *10 | WA-Na | PA | (Oct)$_3$MeN$^+$Cl$^-$ | 30475 | NaOH | P10 | A-210 | 2000 | 2 | **10 | 99% | 3159 | 89.6 |

TABLE 4-continued

| | Step 1 | | | | Step 2 | | | | | Step 3 | | | |
| | Organic solution (A) | | | | In- | | | | | | Organic solution (C) | | |
| | | Hetero | | | | organic | | | | | Epoxy compound | Quaternary salt compound | |
| | Isopoly | atom | Quaternary salt compound | | alkali | Aqueous polymer solution | | | | | Pu- | | Removal |
| Olefin | acid | donor | Kind | ppm | solution | Symbol | Kind | Mn | pH | Kind | rity | ppm | rate |
| Example 26 | *10 | WA-Na | PA | (Oct)$_3$MeN$^+$Cl$^-$ | 30475 | NaOH | P5 | GL366 | 6000 | 2 | **10 | 99% | 4519 | 85.2 |
| Comparative Example 27 | *10 | WA-Na | PA | (Oct)$_3$MeN$^+$Cl$^-$ | 30475 | NaOH | | — | | | **10 | 95% | 28364 | 6.9 |
| Comparative Example 28 | *10 | WA-Na | PA | (Oct)$_3$MeN$^+$Cl$^-$ | 30475 | NaOH | P9 | GL366 | 6000 | 13 | **10 | 95% | 27369 | 10.2 |

Example 27

<Step 1>

Into a test tube equipped with a magnetic stirrer were charged 3.62 g (37.8 mmol) of a 35.5% (by weight) aqueous hydrogen peroxide solution, 0.10 g (0.19 mmol) of methyltrioctyl ammonium chloride, 0.06 g (0.19 mmol) of a sodium tungstate dihydrate, 0.09 g (0.38 mmol) of a 42.5% (by weight) aqueous phosphoric acid solution, and 1.61 g (11.3 mmol) of sodium sulfate, and the mixture was stirred at room temperature for 30 minutes to prepare an aqueous catalyst solution. Then, 5.00 g (37.8 mmol) of a diolefin compound (*11) represented by the following structure and 5.00 g of toluene were added to the aqueous catalyst solution, and the mixture was subjected to oxidation reaction with stirring at 50° C. for 10 hours. Among two phases separated into an aqueous phase and an organic phase after the completion of the reaction, the organic phase was served as an organic solution (A). The remaining amount of the methyltrioctyl ammonium chloride in the organic solution (A) was 21020 ppm.

[Formula 38]

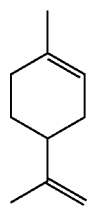

<Step 2>

To the organic solution (A) was added 3.8 g of a 2% aqueous solution of sodium hydroxide (NaOH) corresponding to 10 equivalents relative to the sodium tungstate dihydrate, and the mixture was stirred and allowed to stand to separate it into two phases of an aqueous phase and an organic phase, among which the organic phase was served as an organic solution (B).

<Step 3>

To the organic solution (B) was added 3.8 g of the aqueous polymer solution P1, and the mixture was stirred and allowed to stand to separate it into two phases of an aqueous phase and an organic phase, among which the organic phase was served as an organic solution (C) containing a monoepoxy compound (**11) represented by the following structure. The purity of the monoepoxy compound, and the residual amount and removal rate of the quaternary salt compound are shown in Table 5.

[Formula 39]

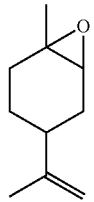

Example 28

An organic solution (C) containing the monoepoxy compound (**11) was obtained in the same manner as in Example 27 except that the methyltrioctyl ammonium chloride (0.10 g, 0.19 mmol) used in the step 1 was replaced by dialkyldimethyl ammonium chloride (a mixture of C8 to C18 alkyl chains) (0.11 g, 0.19 mmol) and the aqueous polymer solution P1 (3.8 g) used in the step 3 was replaced by the aqueous polymer solution P10 (3.8 g). The results are shown in Table 5.

Comparative Example 29

An organic solution (C) containing the monoepoxy compound (**11) was obtained in the same manner as in Example 27 except that the step 3 was omitted. In this comparative example, the organic solution (B) obtained in the step 2 was regarded as the organic solution (C). The results are shown in Table 5.

Comparative Example 30

An organic solution (C) containing the monoepoxy compound (**11) was obtained in the same manner as in Example 27 except that the methyltrioctyl ammonium chloride (0.10 g, 0.19 mmol) used in the step 1 was replaced by dialkyldimethyl ammonium chloride (a mixture of C8 to C18 alkyl chains) (0.11 g, 0.19 mmol). The results are shown in Table 5.

Example 29

<Step 1>

Into a test tube equipped with a magnetic stirrer were charged 9.06 g (94.5 mmol) of a 35.5% (by weight) aqueous hydrogen peroxide solution, 0.17 g (0.38 mmol) of didecyldimethyl ammonium chloride, 0.12 g (0.38 mmol) of a sodium tungstate dihydrate, and 0.26 g (1.13 mmol) of a 42.5% (by weight) aqueous phosphoric acid solution, and 4.03 g (28.4 mmol) of sodium sulfate, and the mixture was stirred at room temperature for 30 minutes to prepare an aqueous catalyst solution. Then, 5.00 g (37.8 mmol) of a diolefin compound (*12) represented by the following structure and 5.00 g of toluene were added to the aqueous catalyst solution, and the mixture was subjected to oxidation reaction with stirring at 50° C. for 10 hours. Among two phases separated into an aqueous phase and an organic phase after the completion of the reaction, the organic phase was served as an organic solution (A). The remaining amount of the didecyldimethyl ammonium chloride in the organic solution (A) was 13258 ppm.

[Formula 40]

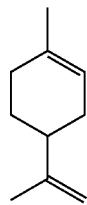

<Step 2>

To the organic solution (A) was added 7.6 g of a 2% aqueous solution of sodium hydroxide (NaOH) corresponding to 10 equivalents relative to the sodium tungstate dihydrate, and the mixture was stirred and allowed to stand to separate it into two phases of an aqueous phase and an organic phase, among which the organic phase was served as an organic solution (B).

<Step 3>

To the organic solution (B) was added 6.9 g of the aqueous polymer solution P1, and the mixture was stirred and allowed to stand to separate it into two phases of an aqueous phase and an organic phase, among which the organic phase was served as an organic solution (C) containing a diepoxy compound (**12) represented by the following structure. The purity of the diepoxy compound, and the residual amount and removal rate of the quaternary salt compound are shown in Table 5.

[Formula 41]

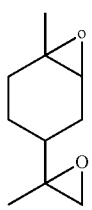

Example 30

An organic solution (C) containing the diepoxy compound (**12) was obtained in the same manner as in Example 29 except that the aqueous polymer solution P1 (6.9 g) used in the step 3 was replaced by the aqueous polymer solution P6 (6.9 g). The results are shown in Table 5.

Comparative Example 31

An organic solution (C) containing the diepoxy compound (**12) was obtained in the same manner as in Example 29 except that the step 3 was omitted. In this comparative example, the organic solution (B) obtained in the step 2 was regarded as the organic solution (C). The results are shown in Table 5.

Comparative Example 32

An organic solution (C) containing the diepoxy compound (**12) was obtained in the same manner as in Example 29 except that the aqueous polymer solution P1 (6.9 g) used in the step 3 was replaced by the aqueous polymer solution P4 (6.9 g). The results are shown in Table 5.

Example 31

<Step 1>

Into a test tube equipped with a magnetic stirrer were charged 3.11 g (32.4 mmol) of a 35.5% (by weight) aqueous hydrogen peroxide solution, 0.08 g (0.16 mmol) of methyltrioctyl ammonium chloride, 0.05 g (0.16 mmol) of a sodium tungstate dihydrate, and 0.07 g (0.32 mmol) of a 42.5% (by weight) aqueous phosphoric acid solution, and 1.38 g (9.72 mmol) of sodium sulfate, and the mixture was stirred at room temperature for 30 minutes to prepare an aqueous catalyst solution. Then, 5.00 g (32.4 mmol) of a monoolefin compound (*13) represented by the following structure and 5.00 g of toluene were added to the aqueous catalyst solution, and the mixture was subjected to oxidation reaction with stirring at 50° C. for 10 hours. Among two phases separated into an aqueous phase and an organic phase after the completion of the reaction, the organic phase was served as an organic solution (A). The remaining amount of the methyltrioctyl ammonium chloride in the organic solution (A) was 29963 ppm.

[Formula 42]

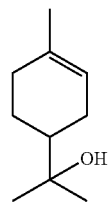

<Step 2>

To the organic solution (A) was added 3.2 g of a 2% aqueous solution of sodium hydroxide (NaOH) corresponding to 10 equivalents relative to the sodium tungstate dihydrate, and the mixture was stirred and allowed to stand to separate it into two phases of an aqueous phase and an organic phase, among which the organic phase was served as an organic solution (B).

<Step 3>

To the organic solution (B) was added 3.3 g of the aqueous polymer solution P1, and the mixture was stirred and allowed to stand to separate it into two phases of an aqueous phase and an organic phase, among which the organic phase was served as an organic solution (C) containing a monoepoxy compound (**13) represented by the following structure. The purity of the monoepoxy compound, and the residual amount and removal rate of the quaternary salt compound are shown in Table 5.

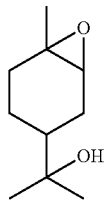

[Formula 43]

Example 32

An organic solution (C) containing the monoepoxy compound (**13) was obtained in the same manner as in Example 31 except that the aqueous polymer solution P1 (3.30 g) used in the step 3 was replaced by the aqueous polymer solution P14 (3.30 g). The results are shown in Table 5.

Example 33

An organic solution (C) containing the monoepoxy compound (**13) was obtained in the same manner as in Example 31 except that the methyltrioctyl ammonium chloride (0.08 g, 0.16 mmol) used in the step 1 was replaced by dialkyldimethyl ammonium chloride (a mixture of C8 to C18 alkyl chains) (0.09 g, 0.16 mmol) and the aqueous polymer solution P1 (3.30 g) used in the step 3 was replaced by the aqueous polymer solution P2 (3.60 g). The results are shown in Table 5.

Example 34

An organic solution (C) containing the monoepoxy compound (**13) was obtained in the same manner as in Example 31 except that the methyltrioctyl ammonium chloride (0.08 g, 0.16 mmol) used in the step 1 was replaced by dialkildimethyl ammonium chloride (a mixture of C8 to C18 alkyl chains) (0.09 g, 0.16 mmol) and the aqueous polymer solution P1 (3.30 g) used in the step 3 was replaced by the aqueous polymer solution P7 (3.60 g). The results are shown in Table 5.

Comparative Example 33

An organic solution (C) containing the monoepoxy compound (**13) was obtained in the same manner as in Example 31 except that the step 3 was omitted. In this comparative example, the organic solution (B) obtained in the step 2 was regarded as the organic solution (C). The results are shown in Table 5.

Comparative Example 34

An organic solution (C) containing the monoepoxy compound (**13) was obtained in the same manner as in Example 31 except that the aqueous polymer solution P1 (3.30 g) used in the step 3 was replaced by the aqueous polymer solution P4 (3.60 g). The results are shown in Table 5.

Comparative Example 35

An organic solution (C) containing the monoepoxy compound (**13) was obtained in the same manner as in Example 31 except that the methyltrioctyl ammonium chloride (0.08 g, 0.16 mmol) used in the step 1 was replaced by dialkildimethyl ammonium chloride (a mixture of C8 to C18 alkyl chains) (0.09 g, 0.16 mmol) and the step 3 was omitted. In this comparative example, the organic solution (B) obtained in the step 2 was regarded as the organic solution (C). The results are shown in Table 5.

Comparative Example 36

An organic solution (C) containing the monoepoxy compound (**13) was obtained in the same manner as in Example 31 except that the methyltrioctyl ammonium chloride (0.08 g, 0.16 mmol) used in the step 1 was replaced by dialkildimethyl ammonium chloride (a mixture of C8 to C18 alkyl chains) (0.09 g, 0.16 mmol) and the aqueous polymer solution P1 (3.30 g) used in the step 3 was replaced by the aqueous polymer solution P3 (3.60 g). The results are shown in Table 5.

Example 35

<Step 1>

Into a test tube equipped with a magnetic stirrer were charged 3.11 g (32.4 mmol) of a 35.5% (by weight) aqueous hydrogen peroxide solution, 0.07 g (0.16 mmol) of didecyldimethyl ammonium chloride, 0.05 g (0.16 mmol) of a sodium tungstate dihydrate, and 0.07 g (0.32 mmol) of a 42.5% (by weight) aqueous phosphoric acid solution, and 1.38 g (9.72 mmol) of sodium sulfate, and the mixture was stirred at room temperature for 30 minutes to prepare an aqueous catalyst solution. Then, 5.00 g (32.4 mmol) of a monoolefin compound (*14) represented by the following structure and 5.00 g of toluene were added to the aqueous catalyst solution, and the mixture was subjected to oxidation reaction with stirring at 50° C. for 10 hours. Among two phases separated into an aqueous phase and an organic phase after the completion of the reaction, the organic phase was served as an organic solution (A). The remaining amount of the didecyldimethyl ammonium chloride in the organic solution (A) was 20917 ppm.

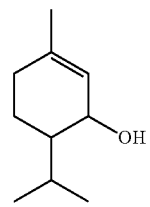

[Formula 44]

<Step 2>

To the organic solution (A) was added 3.20 g of a 2% aqueous solution of sodium hydroxide (NaOH) corresponding to 10 equivalents relative to the sodium tungstate dihydrate, and the mixture was stirred and allowed to stand to separate it into two phases of an aqueous phase and an organic phase, among which the organic phase was served as an organic solution (B).

<Step 3>

To the organic solution (B) was added 2.90 g of the aqueous polymer solution P1, and the mixture was stirred and allowed to stand to separate it into two phases of an aqueous phase and an organic phase, among which the organic phase was served as an organic solution (C) containing a monoepoxy compound (**14) represented by the following structure. The purity of the monoepoxy compound, and the residual amount and removal rate of the quaternary salt compound are shown in Table 5.

[Formula 45]

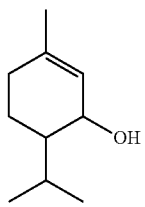

Comparative Example 37

An organic solution (C) containing the monoepoxy compound (**14) was obtained in the same manner as in Example 35 except that the step 3 was omitted. In this comparative example, the organic solution (B) obtained in the step 2 was regarded as the organic solution (C). The results are shown in Table 5.

Comparative Example 38

An organic solution (C) containing the monoepoxy compound (**14) was obtained in the same manner as in Example 35 except that the aqueous polymer solution P1 (2.90 g) used in the step 3 was replaced by the aqueous polymer solution P4 (2.90 g). The results are shown in Table 5.

TABLE 5

| | Step 1 | | | | | Step 2 | Step 3 | | | | | | | |
|---|---|---|---|---|---|---|---|---|---|---|---|---|---|---|
| | Organic solution (A) | | | | | In-organic alkali solution | Aqueous polymer solution | | | | Organic solution (C) | | | |
| | | | | | | | | | | | Epoxy compound | | Quaternary salt compound | |
| | Ole-fin | Isopoly acid | Hetero atom donor | Quaternary salt compound | | | Symbol | Kind | Mn | pH | Kind | Purity | ppm | Removal rate |
| | | | | Kind | ppm | | | | | | | | | |
| Example 27 | *11 | WA-Na | PA | (Oct)₃MeN⁺Cl⁻ | 21020 | NaOH | P1 | A-10SL | 6000 | 3 | **11 | 83% | 2140 | 89.8 |
| Example 28 | *11 | WA-Na | PA | R₂(Me)₂N⁺Cl⁻(R = C8-18) | 21604 | NaOH | P10 | A-210 | 2000 | 2 | **11 | 83% | 2795 | 87.1 |
| Comparative Example 29 | *11 | WA-Na | PA | (Oct)₃MeN⁺Cl⁻ | 21020 | NaOH | — | | | | **11 | 79% | 20891 | 0.6 |
| Comparative Example 30 | *11 | WA-Na | PA | R₂(Me)₂N⁺Cl⁻(R = C8-18) | 21604 | NaOH | — | | | | **11 | 79% | 21281 | 1.5 |
| Example 29 | *12 | WA-Na | PA | (Decyl)₂(Me)₂N⁺Cl⁻ | 13258 | NaOH | P1 | A-10SL | 6000 | 3 | **12 | 77% | 3884 | 70.7 |
| Example 30 | *12 | WA-Na | PA | (Decyl)₂(Me)₂N⁺Cl⁻ | 13258 | NaOH | P6 | GL366 | 6000 | 3 | **12 | 77% | 4665 | 64.8 |
| Comparative Example 31 | *12 | WA-Na | PA | (Decyl)₂(Me)₂N⁺Cl⁻ | 13258 | NaOH | — | | | | **12 | 75% | 13129 | 1.0 |
| Comparative Example 32 | *12 | WA-Na | PA | (Decyl)₂(Me)₂N⁺Cl⁻ | 13258 | NaOH | P4 | A-10SL | 6000 | 13 | **12 | 75% | 11748 | 11.4 |
| Example 31 | *13 | WA-Na | PA | (Oct)₃MeN⁺Cl⁻ | 29963 | NaOH | P1 | A-10SL | 6000 | 3 | **13 | 79% | 1465 | 95.1 |
| Example 32 | *13 | WA-Na | PA | (Oct)₃MeN⁺Cl⁻ | 29963 | NaOH | P14 | DL453 | 50000 | 3 | **13 | 79% | 3457 | 88.6 |
| Example 33 | *13 | WA-Na | PA | R₂(Me)₂N⁺Cl⁻(R = C8-18) | 23367 | NaOH | P2 | A-10SL | 6000 | 4 | **13 | 98% | 1956 | 91.6 |
| Example 34 | *13 | WA-Na | PA | R₂(Me)₂N⁺Cl⁻(R = C8-18) | 23367 | NaOH | P7 | GL366 | 6000 | 4 | **13 | 98% | 2008 | 91.4 |
| Comparative Example 33 | *13 | WA-Na | PA | (Oct)₃MeN⁺Cl⁻ | 29963 | NaOH | — | | | | **13 | 76% | 26946 | 13.4 |
| Comparative Example 34 | *13 | WA-Na | PA | (Oct)₃MeN⁺Cl⁻ | 29963 | NaOH | P4 | A-10SL | 6000 | 13 | **13 | 76% | 26789 | 10.6 |
| Comparative Example 35 | *13 | WA-Na | PA | R₂(Me)₂N⁺Cl⁻(R = C8-18) | 23367 | NaOH | — | | | | **13 | 96% | 23315 | 0.2 |
| Comparative Example 36 | *13 | WA-Na | PA | R₂(Me)₂N⁺Cl⁻(R = C8-18) | 23367 | NaOH | P3 | A-10SL | 6000 | 12 | **13 | 96% | 23149 | 0.9 |
| Example 35 | *14 | WA-Na | PA | (Decyl)₂(Me)₂N⁺Cl⁻ | 20917 | NaOH | P1 | A-10SL | 6000 | 3 | **14 | 83% | 2486 | 88.1 |
| Example 36 | *14 | WA-Na | PA | (Decyl)₂(Me)₂N⁺Cl⁻ | 20917 | NaOH | P6 | GL366 | 6000 | 3 | **14 | 83% | 2991 | 85.7 |
| Comparative Example 37 | *14 | WA-Na | PA | (Decyl)₂(Me)₂N⁺Cl⁻ | 20917 | NaOH | — | | | | **14 | 80% | 18723 | 10.5 |
| Comparative Example 38 | *14 | WA-Na | PA | (Decyl)₂(Me)₂N⁺Cl⁻ | 20917 | NaOH | P4 | A-10SL | 6000 | 13 | **14 | 80% | 19564 | 6.5 |

Example 36

An organic solution (C) containing the monoepoxy compound (**14) was obtained in the same manner as in Example 35 except that the aqueous polymer solution P1 (2.90 g) used in the step 3 was replaced by the aqueous polymer solution P6 (2.90 g). The results are shown in Table 5.

Example 37

<Step 1>

Into a test tube equipped with a magnetic stirrer were charged 3.52 g (36.7 mmol) of a 35.5% (by weight) aqueous hydrogen peroxide solution, 0.10 g (0.18 mmol) of dialkildimethyl ammonium chloride (a mixture of C8 to C18 alkyl chains), 0.06 g (0.18 mmol) of a sodium tungstate dihydrate, 0.08 g (0.37 mmol) of a 42.5% (by weight) aqueous phosphoric acid solution, and 1.56 g (11.0 mmol) of sodium sulfate, and the mixture was stirred at room temperature for 30 minutes to prepare an aqueous catalyst solution. Then, 5.00 g (36.7 mmol) of a monoolefin compound (*15) represented by the following structure and 5.00 g of toluene were added to the aqueous catalyst solution, and the mixture was subjected to oxidation reaction with stirring at 50° C. for 10 hours. Among two phases separated into an aqueous phase and an organic phase after the completion of the reaction, the organic phase was served as an organic solution (A). The remaining amount of the dialkildimethyl ammonium chloride in the organic solution (A) was 26111 ppm.

[Formula 46]

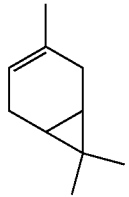

<Step 2>
To the organic solution (A) was added 3.70 g of a 2% aqueous solution of sodium hydroxide (NaOH) corresponding to 10 equivalents relative to the sodium tungstate dihydrate, and the mixture was stirred and allowed to stand to separate it into two phases of an aqueous phase and an organic phase, among which the organic phase was served as an organic solution (B).
<Step 3>
To the organic solution (B) was added 4.10 g of the aqueous polymer solution P14, and the mixture was stirred and allowed to stand to separate it into two phases of an aqueous phase and an organic phase, among which the organic phase was served as an organic solution (C) containing a monoepoxy compound (**15) represented by the following structure. The purity of the monoepoxy compound, and the residual amount and removal rate of the quaternary salt compound are shown in Table 6.

[Formula 47]

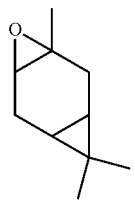

Example 38

An organic solution (C) containing the monoepoxy compound (**15) was obtained in the same manner as in Example 37 except that the aqueous polymer solution P14 (4.10 g) used in the step 3 was replaced by the aqueous polymer solution P6 (4.10 g). The results are shown in Table 6.

Comparative Example 39

An organic solution (C) containing the monoepoxy compound (**15) was obtained in the same manner as in Example 37 except that the step 3 was omitted. In this comparative example, the organic solution (B) obtained in the step 2 was regarded as the organic solution (C). The results are shown in Table 6.

Comparative Example 40

An organic solution (C) containing the monoepoxy compound (**15) was obtained in the same manner as in Example 37 except that the aqueous polymer solution P14 (4.10 g) used in the step 3 was replaced by the aqueous polymer solution P16 (4.10 g). The results are shown in Table 6.

Example 39

<Step 1>
Into a test tube equipped with a magnetic stirrer were charged 3.51 g (36.7 mmol) of a 35.5% (by weight) aqueous hydrogen peroxide solution, 0.33 g (0.73 mmol) of didecyldimethyl ammonium chloride, 0.24 g (0.73 mmol) of a sodium tungstate dihydrate, 0.42 g (1.84 mmol) of a 42.5% (by weight) aqueous phosphoric acid solution, and 1.56 g (11.0 mmol) of sodium sulfate, and the mixture was stirred at room temperature for 30 minutes to prepare an aqueous catalyst solution. Then, 5.00 g (36.7 mmol) of a diolefin compound (*17) represented by the following structure and 5.00 g of toluene were added to the aqueous catalyst solution, and the mixture was subjected to oxidation reaction with stirring at 50° C. for 10 hours. Among two phases separated into an aqueous phase and an organic phase after the completion of the reaction, the organic phase was served as an organic solution (A). The remaining amount of the didecyldimethyl ammonium chloride in the organic solution (A) was 18611 ppm.

[Formula 48]

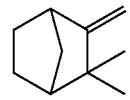

<Step 2>
To the organic solution (A) was added 14.7 g of a 2% aqueous solution of sodium hydroxide (NaOH) corresponding to 10 equivalents relative to the sodium tungstate dihydrate, and the mixture was stirred and allowed to stand to separate it into two phases of an aqueous phase and an organic phase, among which the organic phase was served as an organic solution (B).
<Step 3>
To the organic solution (B) was added 13.3 g of the aqueous polymer solution P1, and the mixture was stirred and allowed to stand to separate it into two phases of an aqueous phase and an organic phase, among which the organic phase was served as an organic solution (C) containing a monoepoxy compound (**17) represented by the following structure. The purity of the monoepoxy compound, and the residual amount and removal rate of the quaternary salt compound are shown in Table 6.

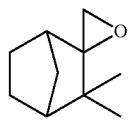

Example 40

An organic solution (C) containing the monoepoxy compound (**17) was obtained in the same manner as in Example 39 except that the aqueous polymer solution P1 (13.3 g) used in the step 3 was replaced by the aqueous polymer solution P6 (13.3 g). The results are shown in Table 6.

Comparative Example 41

An organic solution (C) containing the monoepoxy compound (**17) was obtained in the same manner as in Example 39 except that the step 3 was omitted. In this comparative example, the organic solution (B) obtained in the step 2 was regarded as the organic solution (C). The results are shown in Table 6.

Comparative Example 42

An organic solution (C) containing the monoepoxy compound (**17) was obtained in the same manner as in Example 39 except that the aqueous polymer solution P1 (13.3 g) used in the step 3 was replaced by the aqueous polymer solution P4 (13.3 g). The results are shown in Table 6.

Example 41

<Step 1>
Into a test tube equipped with a magnetic stirrer were charged 3.52 g (36.7 mmol) of a 35.5% (by weight) aqueous hydrogen peroxide solution, 0.33 g (0.73 mmol) of didecyldimethyl ammonium chloride, 2.42 g of a sodium 12-phosphotungstic acid hydrate, and 0.42 g (1.84 mmol) of a 42.5% (by weight) aqueous phosphoric acid solution, and 1.56 g (11.0 mmol) of sodium sulfate, and the mixture was stirred at room temperature for 30 minutes to prepare an aqueous catalyst solution. Then, 5.00 g (36.7 mmol) of a monoolefin compound (*17) represented by the following structure and 5.00 g of toluene were added to the aqueous catalyst solution, and the mixture was subjected to oxidation reaction with stirring at 50° C. for 10 hours. Among two phases separated into an aqueous phase and an organic phase after the completion of the reaction, the organic phase was served as an organic solution (A). The remaining amount of the didecyldimethyl ammonium chloride in the organic solution (A) was 13580 ppm.

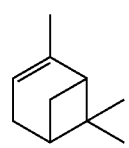

<Step 2>
To the organic solution (A) was added 14.7 g of a 2% aqueous solution of sodium hydroxide (NaOH) corresponding to 10 equivalents relative to the 12-phosphotungstic acid hydrate, and the mixture was stirred and allowed to stand to separate it into two phases of an aqueous phase and an organic phase, among which the organic phase was served as an organic solution (B).

<Step 3>
To the organic solution (B) was added 13.3 g of the aqueous polymer solution P2, and the mixture was stirred and allowed to stand to separate it into two phases of an aqueous phase and an organic phase, among which the organic phase was served as an organic solution (C) containing a monoepoxy compound (**17) represented by the following structure. The purity of the monoepoxy compound, and the residual amount and removal rate of the quaternary salt compound are shown in Table 6.

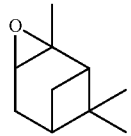

Example 42

An organic solution (C) containing the monoepoxy compound (**17) was obtained in the same manner as in Example 41 except that the aqueous polymer solution P2 (13.3 g) used in the step 3 was replaced by the aqueous polymer solution P15 (13.3 g). The results are shown in Table 6.

Example 43

An organic solution (C) containing the monoepoxy compound (**17) was obtained in the same manner as in Example 41 except that the aqueous polymer solution P2 (13.3 g) used in the step 3 was replaced by the aqueous polymer solution P7 (13.3 g). The results are shown in Table 6.

Comparative Example 43

An organic solution (C) containing the monoepoxy compound (**17) was obtained in the same manner as in Example 41 except that the step 3 was omitted. In this comparative example, the organic solution (B) obtained in the step 2 was regarded as the organic solution (C). The results are shown in Table 6.

Comparative Example 44

An organic solution (C) containing the monoepoxy compound (**17) was obtained in the same manner as in Example 41 except that the aqueous polymer solution P2 (13.3 g) used in the step 3 was replaced by the aqueous polymer solution P4 (13.3 g). The results are shown in Table 6.

Comparative Example 45

An organic solution (C) containing the monoepoxy compound (**17) was obtained in the same manner as in Example 41 except that the step 2 was omitted and the aqueous polymer solution P2 (13.3 g) used in the step 3 was replaced by the aqueous polymer solution P15 (13.3 g). The results are shown in Table 6.

Comparative Example 46

An organic solution (C) containing the monoepoxy compound (**17) was obtained in the same manner as in Example 41 except that the aqueous polymer solution P2 (13.3 g) used in the step 3 was replaced by the aqueous polymer solution P8 (13.3 g). The results are shown in Table 6.

Example 44

<Step 1>

Into a test tube equipped with a magnetic stirrer were charged 3.51 g (36.7 mmol) of a 35.5% (by weight) aqueous hydrogen peroxide solution, 0.33 g (0.73 mmol) of didecyldimethyl ammonium chloride, 0.24 g (0.73 mmol) of a sodium tungstate dihydrate, 0.42 g (1.83 mmol) of a 42.5% (by weight) aqueous phosphoric acid solution, and 1.56 g (11.0 mmol) of sodium sulfate, and the mixture was stirred at room temperature for 30 minutes to prepare an aqueous catalyst solution. Then, 5.00 g (36.7 mmol) of a monoolefin compound (*18) represented by the following structure and 5.00 g of toluene were added to the aqueous catalyst solution, and the mixture was subjected to oxidation reaction with stirring at 50° C. for 10 hours. Among two phases separated into an aqueous phase and an organic phase after the completion of the reaction, the organic phase was served as an organic solution (A). The remaining amount of the didecyldimethyl ammonium chloride in the organic solution (A) was 11586 ppm.

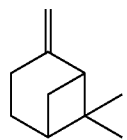

[Formula 52]

<Step 2>

To the organic solution (A) was added 14.7 g of a 2% aqueous solution of sodium hydroxide (NaOH) corresponding to 10 equivalents relative to the sodium tungstate dihydrate, and the mixture was stirred and allowed to stand to separate it into two phases of an aqueous phase and an organic phase, among which the organic phase was served as an organic solution (B).

<Step 3>

To the organic solution (B) was added 13.3 g of the aqueous polymer solution P1, and the mixture was stirred and allowed to stand to separate it into two phases of an aqueous phase and an organic phase, among which the organic phase was served as an organic solution (C) containing a monoepoxy compound (**18) represented by the following structure. The purity of the monoepoxy compound, and the residual amount and removal rate of the quaternary salt compound are shown in Table 6.

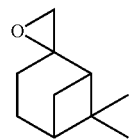

[Formula 53]

Example 45

An organic solution (C) containing the monoepoxy compound (**18) was obtained in the same manner as in Example 44 except that the aqueous polymer solution P1 (13.3 g) used in the step 3 was replaced by the aqueous polymer solution P6 (13.3 g). The results are shown in Table 6.

Comparative Example 47

An organic solution (C) containing the monoepoxy compound (**18) was obtained in the same manner as in Example 44 except that the step 3 was omitted. In this comparative example, the organic solution (B) obtained in the step 2 was regarded as the organic solution (C). The results are shown in Table 6.

Comparative Example 48

An organic solution (C) containing the monoepoxy compound (**18) was obtained in the same manner as in Example 44 except that the aqueous polymer solution P1 (13.3 g) used in the step 3 was replaced by the aqueous polymer solution P4 (13.3 g). The results are shown in Table 6.

TABLE 6

| | Step 1 | | | | | Step 2 | Step 3 | | | | | | |
|---|---|---|---|---|---|---|---|---|---|---|---|---|---|
| | Organic solution (A) | | | | | In- | | | | | Organic solution (C) | | |
| | | | Hetero | | | organic | | | | | Epoxy compound | Quaternary salt compound | |
| | Ole-fin | Isopoly acid | atom donor | Quaternary salt compound | | alkali solution | Aqueous polymer solution | | | | Pu-rity | | Removal |
| | | | | Kind | ppm | | Symbol | Kind | Mn | pH | | ppm | rate |
| Example 37 | *15 | WA-Na | PA | R₂(Me)₂N⁺Cl⁻(R = C8-18) | 26111 | NaOH | P14 | DL453 | 50000 | 3 | **15 94% | 1834 | 93.0 |
| Example 38 | *15 | WA-Na | PA | R₂(Me)₂N⁺Cl⁻(R = C8-18) | 26111 | NaOH | P6 | GL366 | 6000 | 3 | **15 94% | 1462 | 94.4 |
| Comparative Example 39 | *15 | WA-Na | PA | R₂(Me)₂N⁺Cl⁻(R = C8-18) | 26111 | NaOH | | — | | | **15 92% | 25493 | 2.4 |
| Comparative Example 40 | *15 | WA-Na | PA | R₂(Me)₂N⁺Cl⁻(R = C8-18) | 26111 | NaOH | P16 | DL453 | 50000 | 13 | **15 92% | 25113 | 3.8 |
| Example 39 | *16 | WA-Na | PA | (Decyl)₂(Me)₂N⁺Cl⁻ | 18611 | NaOH | P1 | A-10SL | 6000 | 3 | **16 80% | 4832 | 74.0 |

TABLE 6-continued

| | | Step 1 | | | | Step 2 | Step 3 | | | | | | |
|---|---|---|---|---|---|---|---|---|---|---|---|---|---|
| | | Organic solution (A) | | | | In- | | | | | Organic solution (C) | | |
| | | | Hetero | | | organic | | | | | Epoxy compound | | Quaternary salt compound |
| | Ole- | Isopoly | atom | Quaternary salt compound | | alkali | Aqueous polymer solution | | | | | Pu- | Removal |
| | fin | acid | donor | Kind | ppm | solution | Symbol | Kind | Mn | pH | Kind | rity | ppm | rate |
| Example 40 | *16 | WA-Na | PA | (Decyl)$_2$(Me)$_2$N$^+$Cl$^-$ | 18611 | NaOH | P6 | GL366 | 6000 | 3 | **16 | 80% | 5787 | 68.9 |
| Comparative Example 41 | *16 | WA-Na | PA | (Decyl)$_2$(Me)$_2$N$^+$Cl$^-$ | 18611 | NaOH | — | | | | **16 | 78% | 18497 | 0.6 |
| Comparative Example 42 | *16 | WA-Na | PA | (Decyl)$_2$(Me)$_2$N$^+$Cl$^-$ | 18611 | NaOH | P4 | A-10SL | 6000 | 13 | **16 | 78% | 12890 | 30.7 |
| Example 41 | *17 | 12-WA | PA | (Decyl)$_2$(Me)$_2$N$^+$Cl$^-$ | 13580 | NaOH | P2 | A-10SL | 6000 | 4 | **17 | 88% | 1996 | 85.3 |
| Example 42 | *17 | 12-WA | PA | (Decyl)$_2$(Me)$_2$N$^+$Cl$^-$ | 13580 | NaOH | P15 | DL453 | 50000 | 4 | **17 | 88% | 2098 | 84.6 |
| Example 43 | *17 | 12-WA | PA | (Decyl)$_2$(Me)$_2$N$^+$Cl$^-$ | 13580 | NaOH | P7 | GL366 | 6000 | 4 | **17 | 88% | 2549 | 81.2 |
| Comparative Example 43 | *17 | 12-WA | PA | (Decyl)$_2$(Me)$_2$N$^+$Cl$^-$ | 13580 | NaOH | — | | | | **17 | 85% | 12499 | 8.0 |
| Comparative Example 44 | *17 | 12-WA | PA | (Decyl)$_2$(Me)$_2$N$^+$Cl$^-$ | 13580 | NaOH | P4 | A-10SL | 6000 | 13 | **17 | 85% | 13004 | 4.2 |
| Comparative Example 45 | *17 | 12-WA | PA | (Decyl)$_2$(Me)$_2$N$^+$Cl$^-$ | 13580 | — | P15 | DL453 | 50000 | 4 | **17 | 85% | 13412 | 1.2 |
| Comparative Example 46 | *17 | 12-WA | PA | (Decyl)$_2$(Me)$_2$N$^+$Cl$^-$ | 13580 | NaOH | P8 | GL366 | 6000 | 12 | **17 | 85% | 12213 | 10.1 |
| Example 44 | *18 | WA-Na | PA | (Decyl)$_2$(Me)$_2$N$^+$Cl$^-$ | 11586 | NaOH | P1 | A-10SL | 6000 | 3 | **18 | 62% | 1048 | 91.0 |
| Example 45 | *18 | WA-Na | PA | (Decyl)$_2$(Me)$_2$N$^+$Cl$^-$ | 11586 | NaOH | P6 | GL366 | 6000 | 3 | **18 | 62% | 1517 | 86.9 |
| Comparative Example 47 | *18 | WA-Na | PA | (Decyl)$_2$(Me)$_2$N$^+$Cl$^-$ | 11586 | NaOH | — | | | | **18 | 68% | 10996 | 5.1 |
| Comparative Example 48 | *18 | WA-Na | PA | (Decyl)$_2$(Me)$_2$N$^+$Cl$^-$ | 11586 | NaOH | P4 | A-10SL | 6000 | 13 | **18 | 68% | 11543 | 0.4 |

In Table 6, 12-WA means 12-phosphotungstic acid hydrate.

Example 46

<Step 1>

Into a test tube equipped with a magnetic stirrer were charged 4.27 g (44.6 mmol) of a 35.5% (by weight) aqueous hydrogen peroxide solution, 0.08 g (0.18 mmol) of didecyldimethyl ammonium chloride, 0.04 g (0.18 mmol) of a tungstic acid, and 0.02 g (0.09 mmol) of a 42.5% (by weight) aqueous phosphoric acid solution, and the mixture was stirred at room temperature for 30 minutes to prepare an aqueous catalyst solution. Then, 5.00 g (35.6 mmol) of a monoolefin compound (*19) represented by the following structure and 5.00 g of toluene were added to the aqueous catalyst solution, and the mixture was subjected to oxidation reaction with stirring at 80° C. for 10 hours. Among two phases separated into an aqueous phase and an organic phase after the completion of the reaction, the organic phase was served as an organic solution (A). The remaining amount of the didecyldimethyl ammonium chloride in the organic solution (A) was 14886 ppm.

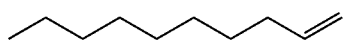

[Formula 54]

<Step 2>

To the organic solution (A) was added 3.60 g of a 2% aqueous solution of sodium hydroxide (NaOH) corresponding to 10 equivalents relative to the tungstic acid, and the mixture was stirred and allowed to stand to separate it into two phases of an aqueous phase and an organic phase, among which the organic phase was served as an organic solution (B).

<Step 3>

To the organic solution (B) was added 3.20 g of the aqueous polymer solution P1, and the mixture was stirred and allowed to stand to separate it into two phases of an aqueous phase and an organic phase, among which the organic phase was served as an organic solution (C) containing a monoepoxy compound (**19) represented by the following structure. The purity of the monoepoxy compound, and the residual amount and removal rate of the quaternary salt compound are shown in Table 7.

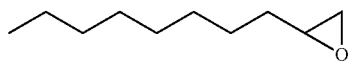

[Formula 55]

Example 47

An organic solution (C) containing the monoepoxy compound (**19) was obtained in the same manner as in Example 46 except that the aqueous polymer solution P1 (3.20 g) used in the step 3 was replaced by the aqueous polymer solution P11 (3.20 g). The results are shown in Table 7.

Example 48

An organic solution (C) containing the monoepoxy compound (**19) was obtained in the same manner as in Example 46 except that the aqueous polymer solution P1 (3.20 g) used in the step 3 was replaced by the aqueous polymer solution P6 (3.20 g). The results are shown in Table 7.

Comparative Example 49

An organic solution (C) containing the monoepoxy compound (**19) was obtained in the same manner as in Example 46 except that the step 3 was omitted. In this comparative example, the organic solution (B) obtained in the step 2 was regarded as the organic solution (C). The results are shown in Table 7.

Comparative Example 50

An organic solution (C) containing the monoepoxy compound (**19) was obtained in the same manner as in Example 46 except that the step 2 was omitted and the organic solution (A) obtained in the step 1 was regarded as the organic solution (B). The results are shown in Table 7.

Comparative Example 51

An organic solution (C) containing the monoepoxy compound (**19) was obtained in the same manner as in Example 46 except that the aqueous polymer solution P1 (3.20 g) used in the step 3 was replaced by the aqueous polymer solution P4 (3.20 g). The results are shown in Table 7.

Example 49

<Step 1>

Into a test tube equipped with a magnetic stirrer were charged 3.58 g (37.1 mmol) of a 35.5% (by weight) aqueous hydrogen peroxide solution, 0.17 g (0.30 mmol) of dialkildimethyl ammonium chloride (a mixture of C8 to C18 alkyl chains), 0.07 g (0.30 mmol) of a tungstic acid, and 0.34 g (1.49 mmol) of a 42.5% (by weight) aqueous phosphoric acid solution, and the mixture was stirred at room temperature for 30 minutes to prepare an aqueous catalyst solution. Then, 5.00 g (29.7 mmol) of a monoolefin compound (*20) represented by the following structure and 5.00 g of toluene were added to the aqueous catalyst solution, and the mixture was subjected to oxidation reaction with stirring at 80° C. for 10 hours. Among two phases separated into an aqueous phase and an organic phase after the completion of the reaction, the organic phase was served as an organic solution (A). The remaining amount of the dialkildimethyl ammonium chloride in the organic solution (A) was 10847 ppm.

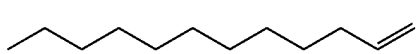

[Formula 56]

<Step 2>

To the organic solution (A) was added 5.90 g of a 2% aqueous solution of sodium hydroxide (NaOH) corresponding to 10 equivalents relative to the tungstic acid, and the mixture was stirred and allowed to stand to separate it into two phases of an aqueous phase and an organic phase, among which the organic phase was served as an organic solution (B).

<Step 3>

To the organic solution (B) was added 6.60 g of the aqueous polymer solution P14, and the mixture was stirred and allowed to stand to separate it into two phases of an aqueous phase and an organic phase, among which the organic phase was served as an organic solution (C) containing a monoepoxy compound (**20) represented by the following structure. The purity of the monoepoxy compound, and the residual amount and removal rate of the quaternary salt compound are shown in Table 7.

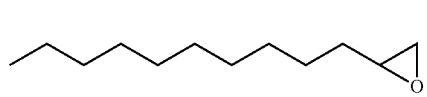

[Formula 57]

Example 50

An organic solution (C) containing the monoepoxy compound (**20) was obtained in the same manner as in Example 49 except that the aqueous polymer solution P14 (6.60 g) used in the step 3 was replaced by the aqueous polymer solution P6 (6.60 g). The results are shown in Table 7.

Comparative Example 52

An organic solution (C) containing the monoepoxy compound (**20) was obtained in the same manner as in Example 49 except that the step 3 was omitted. In this comparative example, the organic solution (B) obtained in the step 2 was regarded as the organic solution (C). The results are shown in Table 7.

Comparative Example 53

An organic solution (C) containing the monoepoxy compound (**20) was obtained in the same manner as in Example 49 except that the aqueous polymer solution P14 (6.60 g) used in the step 3 was replaced by the aqueous polymer solution P16 (6.60 g). The results are shown in Table 7.

Comparative Example 54

An organic solution (C) containing the monoepoxy compound (**20) was obtained in the same manner as in Example 49 except that the step 2 was omitted and the organic solution (A) obtained in the step 1 was regarded as the organic solution (B). The results are shown in Table 7.

TABLE 7

| | Step 1 | | | | | Step 2 | Step 3 | | | | | | |
|---|---|---|---|---|---|---|---|---|---|---|---|---|---|
| | Organic solution (A) | | | | | In- | | | | | Organic solution (C) | | |
| | | | | | | organic | | | | | Epoxy compound | Quaternary salt compound | |
| | | | Hetero atom | Quaternary salt compound | | alkali | Aqueous polymer solution | | | | | | Removal |
| | Olefin | Isopoly acid | donor | Kind | ppm | solution | Symbol | Kind | Mn | pH | Kind | Purity | ppm | rate |
| Example 46 | *19 | WA | PA | (Decyl)₂(Me)₂N⁺Cl⁻ | 14886 | NaOH | P1 | A-10SL | 6000 | 3 | **19 | 94% | 845 | 94.3 |
| Example 47 | *19 | WA | PA | (Decyl)₂(Me)₂N⁺Cl⁻ | 14886 | NaOH | P11 | A-210 | 2000 | 3 | **19 | 94% | 914 | 93.9 |
| Example 48 | *19 | WA | PA | (Decyl)₂(Me)₂N⁺Cl⁻ | 14886 | NaOH | P6 | GL366 | 6000 | 3 | **19 | 94% | 735 | 95.1 |
| Comparative Example 49 | *19 | WA | PA | (Decyl)₂(Me)₂N⁺Cl⁻ | 14886 | NaOH | | — | | | **19 | 90% | 13598 | 8.7 |
| Comparative Example 50 | *19 | WA | PA | (Decyl)₂(Me)₂N⁺Cl⁻ | 14886 | — | P1 | A-10SL | 6000 | 3 | **19 | 90% | 14597 | 1.9 |
| Comparative Example 51 | *19 | WA | PA | (Decyl)₂(Me)₂N⁺Cl⁻ | 14886 | NaOH | P4 | A-10SL | 6000 | 13 | **19 | 90% | 13271 | 10.8 |
| Example 49 | *20 | WA | PA | R₂(Me)₂N⁺Cl⁻(R=C8-18) | 10847 | NaOH | P14 | DL453 | 50000 | 3 | **20 | 95% | 734 | 93.2 |
| Example 50 | *20 | WA | PA | R₂(Me)₂N⁺Cl⁻(R=C8-18) | 10847 | NaOH | P6 | GL366 | 6000 | 3 | **20 | 95% | 648 | 94.0 |
| Comparative Example 52 | *20 | WA | PA | R₂(Me)₂N⁺Cl⁻(R=C8-18) | 10847 | NaOH | | — | | | **20 | 91% | 9798 | 9.7 |
| Comparative Example 53 | *20 | WA | PA | R₂(Me)₂N⁺Cl⁻(R=C8-18) | 10847 | NaOH | P16 | DL453 | 50000 | 13 | **20 | 91% | 9517 | 12.3 |
| Comparative Example 54 | *20 | WA | PA | R₂(Me)₂N⁺Cl⁻(R=C8-18) | 10847 | — | P14 | DL453 | 50000 | 3 | **20 | 91% | 10048 | 7.4 |

In Table 7, WA means tungstic acid.

What is claimed is:

1. A method for producing an epoxy compound comprising the following step 1, step 2, and step 3:
   step 1: a step in which in a mixture liquid containing an olefin compound, an aqueous hydrogen peroxide solution, a quaternary salt compound, a heteropoly acid, and an organic solvent, the olefin compound is subjected to the oxidation reaction to obtain an organic solution (A) containing an epoxy compound,
   step 2: a step in which an aqueous inorganic alkali solution is allowed to contact with the organic solution (A) to obtain an organic solution (B) containing the epoxy compound, and
   step 3: a step in which an acidic aqueous solution containing a polymer having at least one functional group selected from the group consisting of a carboxyl group and a sulfonic acid group is allowed to contact with the organic solution (B) to obtain an organic solution (C) containing the epoxy compound.

2. The production method according to claim 1, wherein the olefin compound is at least one compound selected from the group consisting of a cyclic olefin compound and a long-chain linear olefin compound.

3. The production method according to claim 1, wherein the amount used of the hydrogen peroxide is 0.001 to 10 equivalents per one carbon-carbon double bond contained in the olefin compound.

4. The production method according to claim 1, wherein the quaternary salt compound is a quaternary ammonium salt compound having at least one alkyl group with 6 to 20 carbon atoms in the molecule.

5. The production method according to claim 1, wherein the amount used of the quaternary salt compound is 0.0001 to 20 moles per 100 moles of the olefin compound.

6. The production method according to claim 1, wherein the amount used of the heteropoly acid is 0.0001 to 20 moles per 100 moles of the olefin compound.

7. The production method according to claim 1, wherein the organic solvent is an aromatic hydrocarbon-based organic solvent.

8. The production method according to claim 1, wherein the oxidation reaction is further carried out in the presence of a neutral inorganic salt.

9. The production method according to claim 1, wherein the neutral inorganic salt is a sulfate.

10. The production method according to claim 1, wherein the amount used of the neutral inorganic salt is 1 to 500 moles per 100 moles of the olefin compound.

11. The production method according to claim 1, wherein the polymer having at least one functional group selected from the group consisting of a carboxyl group and a sulfonic acid group is at least one selected from the group consisting of polyacrylic acid, polymaleic acid, polystyrene sulfonic acid, carboxymethyl cellulose and alkali metal salts thereof.

12. The production method according to claim 1, wherein the polymer having at least one functional group selected from the group consisting of a carboxyl group and a sulfonic acid group has a number average molecular weight of 500 to 200,000.

13. The production method according to claim 1, wherein the amount used of the polymer having a carboxyl group and/or a sulfonic acid group is 0.5-to 50-fold weight based on the weight of the quaternary salt compound.

* * * * *